(12) United States Patent
Dawant et al.

(10) Patent No.: US 7,167,760 B2
(45) Date of Patent: Jan. 23, 2007

(54) APPARATUS AND METHODS OF OPTIMAL PLACEMENT OF DEEP BRAIN STIMULATOR

(75) Inventors: Benoit M. Dawant, Nashville, TN (US); Peter E. Konrad, Old Hickory, TN (US); J. Michael Fitzpatrick, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 443 days.

(21) Appl. No.: 10/833,504

(22) Filed: Apr. 28, 2004

(65) Prior Publication Data

US 2005/0004617 A1 Jan. 6, 2005

Related U.S. Application Data

(60) Provisional application No. 60/466,219, filed on Apr. 28, 2003.

(51) Int. Cl.
*A61N 1/05* (2006.01)

(52) U.S. Cl. .......... 607/116; 382/131; 607/45; 607/115; 600/378

(58) Field of Classification Search .......... 382/131; 607/115, 116, 32, 373, 45; 378/4; 600/378, 600/544, 545; 606/129
See application file for complete search history.

(56) References Cited

U.S. PATENT DOCUMENTS

| 6,146,390 | A |  | 11/2000 | Heilbrun et al. |
| 6,253,109 | B1 | * | 6/2001 | Gielen ............ 607/45 |
| 2003/0181954 | A1 | * | 9/2003 | Rezai ............ 607/45 |
| 2003/0228042 | A1 | * | 12/2003 | Sinha ............ 382/131 |
| 2003/0233039 | A1 | * | 12/2003 | Shao et al. ............ 600/407 |
| 2005/0049486 | A1 | * | 3/2005 | Urquhart et al. ............ 600/429 |
| 2005/0228256 | A1 | * | 10/2005 | Labadie et al. ............ 600/407 |
| 2006/0190055 | A1 | * | 8/2006 | Malinowski et al. ......... 607/45 |

FOREIGN PATENT DOCUMENTS

WO  WO 02/093292 A2  11/2002

OTHER PUBLICATIONS

G. Deuschl, J. Volkmann, and P. Krack, "Deep brain stimulation for movement disorders", *Movement Disorders*, vol. 17 (supplement 3), pp. S1-S1, 2002.

B. Schrader, W. Hamel, D. Weinert, and H. M. Mehdom, "Documentation of electrode localization." *Movement Disorders*, vol. 17 (supplement 3), pp. S167-S174, 2002.

J. L. Vitek, Mechanisms of deep brain stimulation: excitation or inhibition. *Movement Disorders*, vol. 17 (supplement 3), pp. S69-S72, 2002.

(Continued)

*Primary Examiner*—Robert E. Pezzuto
*Assistant Examiner*—Erik J Bustamante
(74) *Attorney, Agent, or Firm*—Morris Manning & Martin LLP; Tim Tingkang Xia, Esq.

(57) ABSTRACT

A method of optimal placement of a deep brain stimulator in a targeted region of a brain of a living subject for optimal deep brain stimulation. In one embodiment, the method includes the steps of nonmanually selecting an initial optimal position from, refining the nonmanually selected initial optimal position to determine a final position, and placing the deep brain stimulator at the final position in the targeted region of the brain of the living subject.

24 Claims, 6 Drawing Sheets

OTHER PUBLICATIONS

A. M. Lozano, Deep brain stimulation for Parkinson's disease. vol. 7, No. 3, pp. 199-203, 2001.

R. L. Galloway and R. J. Maciunas, "Stereotactic neurosurgery", *Crit Rev Biomed Eng*, vol. 18, No. 3, pp. 181-205, 1990.

J. Franck, P. Konrad, R. Franklin, F. Haer and D. Hawksley. "STarFix: A Novel Approach to Frameless Stereotactic Neurosurgery Utilizing a Miniaturized Customized Pretargeted Cranial Platform Fixture—Technical Description, Unique Features, and Case Reports", *Movement Disorders Society*, 7th Intl. Congress of Parkinsons Disease & Movement Disorder, Miami, FL, Nov. 2002.

C. R. Maurer, Jr., J. M. Fitzpatrick, M. Y. Wang, R. L. Galloway, Jr., R. J. Maciunas, and G. S. Allen, "Registration of head volume images using implantable fiducial markers," *IEEE Trans. Med. Imaging*, vol. 16, pp. 447-462, 1997.

J. P. Thirion, "Image matching as a diffusion process: an analogy with Maxwell's demons". *Medical Image Analysis*, vol. 2, No. 3, pp. 243-260, 1998.

G. Rhode, A. Aldroubi and B. M. Dawant, "The Adaptive-bases algorithm for intensity-based nonrigid image registration," *IEEE Transactions on Medical Imaging*, vol. 22, No. 11, pp. 1470-1479, 2003.

D. Rueckert, L. I. Sonoda, C. Hayes, D. L. G. Hill, M. O. Leach, and D. J. Hawkes, "Nonrigid Registration Using Free-Form Deformations: Application to Breast MR Images." *IEEE Transactions on Medical Imaging*, vol. 18, No. 8, pp. 712-721, 1999.

C. R. Meyer, J. L. Boes, B. Kim, P. Bland, K. R. Zasadny, P. V. Kison, K. Koral, K. A. Frey, and R. L. Wahl., "Demonstration of accuracy and clinical versatility of mutual information for automatic multimodality image fusion using affine and thin-plate" *Medical Image Analysis*, vol. 3, pp. 195-206, 1997.

F. Maes, A. Collignon, and P. Suetens, "Multimodality image registration by maximization of mutual information," *IEEE Transaction on Medical Imaging* vol. 16, No. 2, pp. 187-198, 1997.

J.D. Atkinson, D. L. Collins, G. Bertrand, T. M. Peters, G. B. Pike, and A. F. Sadikot, "Optimal location of thalamotomy lesions for tremor associated with Parkinson Disease: a probabilistic analysis based on postoperative magnetic resonance imaging and an integrated digital atlas", *J. Neurosurgery*, vol. 96, pp. 854-866, 2002.

G. Schaltenbrand and W. Wahren, *Atlas for Stereotaxy of the Human Brain*. Stuttgart, Germany: Thieme, 1977.

K. W. Finnis, Y. P. Starreveld, A. G. Parrent, A. F. Sadikot, and T. M. Peters, "Threedimensional database of dubcortical dlectrophysiology for dmage-guided stereotactic functional neurosurgery", *IEEE Transactions on Medical Imaging*, vol. 22 (11), pp. 93-104, 2003.

J. Talairach and P. Tourneau, *Co-Planar Stereotaxic Atlas of the Human Brain*. Stuttgart, Germany: Georg Thieme Verlag, 1988.

P. St-Jean, A. F. Sadikot, D. L. Collins, D. Clonda, R. Kasrai, A. C. Evans, and T. M. Peters, "Automated atlas integration and interactive 3-dimensional visualization tools for planning and guidance in functional neurosurgery," *IEEE Trans. Med. Imag.*, vol. 17, pp. 672-680, 1998.

G. Deuschl, J. Volkmann, P. Krack, "Deep brain stimulation for movement disorders", *Movement Disorders*, vol. 17 (supplement 3) pp. S1-S1, 2002.

Deuschl, G., et al., "Deep brain stimulation of the subthalamic nucleus for Parkinson's disease: a therapy approaching evidence-based standards." *J. Neurol*, 2003. 250 Suppl 1: p. 143-146.

B. Horn and B. Schunck, "Determining optical flow", *Artificial Intelligence*, vol. 17, pp. 185-203, 1981.

D.J. Burr, "A dynamic model for image registration." *Computer Graphics and Image Processing*, vol. 15, pp. 102-112, 1981.

C. Nickele, E. Cetinkaya, J. Michael Fitzpatrick, and P.E. Konrad. "Method for Placing Deep-Brain Stimulators ", Proceedings of *Medical Imaging 2003: Image Processing*, SPIE, (in press).

\* cited by examiner

APPARATUS AND METHODS OF OPTIMAL PLACEMENT OF DEEP BRAIN STIMULATOR

CROSS-REFERENCE TO RELATED PATENT APPLICATION

This application claims the benefit, pursuant to 35 U.S.C. §119(e), of provisional U.S. Patent Application Ser. No. 60/466,219, filed Apr. 28, 2003, entitled "APPARATUS AND METHODS OF COMPUTERIZED ATLAS-GUIDED POSITIONING OF DEEP BRAIN STIMULATORS," by Benoit M. Dawant, which is incorporated herein by reference in its entirety.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference. In terms of notation, hereinafter, "[n]" represents the nth reference cited in the reference list. For example, [9] represents the 9th reference cited in the reference list, namely, G. Rhode, A. Aldroubi and B. M. Dawant, "The Adaptive-bases algorithm for intensity-based nonrigid image registration," *IEEE Transactions on Medical Imaging*, vol. 22, no. 11, pp 1470–1479, 2003.

FIELD OF THE INVENTION

The present invention generally relates to deep brain stimulation in a targeted region of a brain of a living subject, and in particular to the utilization of an atlas to nonmanually select an initial optimal position from which a final position of a deep brain stimulator that is to be implanted in the targeted region is determined.

BACKGROUND OF THE INVENTION

Since its first Food and Drug Administration (FDA) approval in 1998, deep-brain stimulation (DBS) has gained significant popularity in the treatment of a variety of brain-controlled disorders, including movement disorders [1, 2]. The therapy of the DBS has significant applications in the treatment of tremor, rigidity, and drug induced side effects in patients with Parkinson's disease and essential tremor. Generally, such treatment involves placement of a DBS electrode lead through a burr hole drilled in the patient's skull, followed by placement of the electrode lead and then applying appropriate stimulation signals through the electrode lead to the physiological target. The placement portion of the treatment, involving stereotactic neurosurgical methodology, is very critical, and has been the subject of much attention and research. In particular, finding the deep brain target and then permanently placing the electrode lead so that it efficiently stimulates such target is very important.

Finding the optimal physiological target in deep brain stimulation implants for the treatment of movement disorders is a particularly complicated task. This is especially true for the treatment of symptoms that cannot be tested at the operating table during the electrode lead implantation. For instance, it is practically impossible to test walking and postural stability in Parkinson's Disease (PD) patients during the DSB lead implantation. Two other major PD symptoms, Rigidity and Akinesia, are also considered difficult to evaluate quantitatively during DBS lead implantation. On the other hand, the surgical targets of interest involve deep brain nuclei or subregions within the subthalamus or globus pallidus internus. These structures are not visible in any current imaging modalities, such as magnetic resonance imaging (MRI), X-ray computed tomography (CT), or Positron Emission Tomography (PET).

Ideally, the optimal target for the DBS therapy should be located within the stimulation range of 1 or 2 contacts, each contact measuring 1.5 mm separated by either 1.5 mm or 0.5. Effective stimulation results when the contacts surround the optimal target [3, 4]. For example, for placement of a 4-contact electrode lead of a deep brain stimulator 100, which has a tip portion 170, a central body portion 150 and associated contacts 110, 120, 130 and 140 as shown in FIG. 1, (Medtronic #3387 or #3389 *quadripolar lead*®, Medtronic, Inc., Minneapolis, Minn.), in the proximity of functional areas which one may refer to as targets or targeted regions, a preferable scenario is that two contacts 110 and 120 of the quadripolar lead 100 lie above and the other contacts 130 and 140 lie below a target. For this example of the lead, each contact 110 (120, 130, 140) has a length, $d_1$, which is substantially around 1.5 mm for a Medtronic #3387 or #3389 quadripolar lead, and the distance between two neighboring contacts, for example, 130 and 140, is $d_2$, where $d_2=1.5$ mm for Medtronic #3387 quadripolar lead, and $d_2=0.5$ mm for Medtronic #3389 quadripolar lead, respectively. If the contacts are located as little as 2 mm away from the desired target, ineffective stimulation results due to several reasons: (i) failure to capture control of the group of neurons, (ii) stimulation of non-desirable areas resulting in unpleasant stimulation, or (iii) necessity for higher stimulus intensities to produce the desired effect resulting in reduced battery life of the implantation, or an any combination of these or other reasons. At least for these reasons, targeting the specific neurons of interest for this therapy requires millimetric precision and allowance for variability among patients. Therefore, the process of implantation of a DBS electrode lead requires stereotactic neurosurgical methodology, i.e., the use of a common reference coordinate system to target structures within the brain. Typically, the process of implantation of a DBS electrode follows a step-wise progression of (i) initial estimation of target localization based on imaged anatomical landmarks, (ii) intra-operative microanatomical mapping of key features associated with the intended target of interest, (iii) adjustment of the final target of implantation by appropriate shifts in three dimensional space, and (iv) implantation of a quadripolar electrode with contacts located surrounding the final desired target.

Because of the invisibility of deep brain targets of interest in any current imaging modalities, such as MRI, CT, or PET, the location of these targets can only be inferred approximately from the position of adjacent structures that are visible in the images. To augment the information that these images provide, printed anatomic atlases or electronic versions of these have been used. Anatomic atlases, such as the Schaltenbrand-Wahren atlas [14], involve a series of unevenly spaced brain sections that have been histologically stained to reveal the structures and substructures of interest. When digitized, these atlases can be superimposed on the pre-operative images using landmarks visible both in the atlas and in the image volumes. Although it represents a partial solution to the target identification problem, this approach suffers from a number of shortcomings [15]. First, available anatomic atlases have been created from one single brain [16] or from several hemispheres pertaining to different individuals [14]. When a single brain is used, information is limited to one sectioning plane per hemisphere. When several brains are used, these atlases show non-contiguous anatomy in intersecting orthogonal slices. Registration (i.e. spatial alignment) of these atlases to the image volumes also raises a number of issues. The standard procedure is to register atlas and image volumes using the inter commisural anterior commissure (AC)-posterior commissure (PC) reference system. This method is one in which the anterior commissure (AC) and posterior commissure (PC) points are manually selected in the images. The volumes are first translated to align the AC points. They are then rotated to align the AC-PC line and the midsagittal planes. Unfortunately, this technique results in substantial misregistration errors. A better approach proposed by St-Jean et al. [17] involves digitizing the Schaltenbrand-Wahren atlas, stacking individual slices, and creating 3D structures from these slices through interpolation. These 3D structures are then registered to one MR image volume by identifying homologous landmarks, thus creating an MR volume on which labels from the atlas can be projected. But, this procedure only guarantees that the landmarks are registered to each other. In a later publication [15], the authors acknowledge that this limitation plus the fact that the creation of the 3D structures involves interpolating 2D atlas slices that can be between 0.5 and 3 mm apart limit the accuracy and therefore the clinical usefulness of this approach.

In current clinical practice, the initial target localization is manually selected on magnetic resonance (MR) images based on anterior commissural (AC)-posterior commissural (PC) coordinates. It can be a lengthy process (sometimes extending for hours in an awake patient) and it requires expertise in neurosurgery, neurophysiology, and clinical neurology [18, 19]. This combined expertise is available only at a limited number of sites, which limits access to the procedure to about 3000 patients per year despite the estimated 180,000 patients per year who would benefit from it in the United States alone.

Therefore, a heretofore unaddressed need exists in the art to address the aforementioned deficiencies and inadequacies.

SUMMARY OF THE INVENTION

In one aspect, the present invention relates to a method for optimal placement of a deep brain stimulator in a targeted region of a brain of a living subject, where the deep brain stimulator includes a plurality of contact-electrodes. In one embodiment, the method includes the step of nonmanually selecting an initial optimal position in the target region, finding a final position from the nonmanually selected initial optimal position and placing the deep brain stimulator at the final position in the targeted region of the brain of the living subject. The selecting step is carried out pre-operatively, while the finding step and the placing step are carried out intra-operatively.

The step of nonmanually selecting the initial optimal position includes the step of choosing an image volume as a common volume of reference from a set of image volumes. The set of image volumes has N image volumes, and each is acquired pre-operatively from a brain of a living subject having a deep brain stimulator placed in a target, where N is an integer greater than 2. The nonmanually selecting step further includes the steps of registering each of the remaining N−1 image volumes to the chosen common volume of reference by a nonrigid registration algorithm so as to create an atlas, and mapping spatial coordinates of the deep brain stimulator in each of the remaining N−1 image volumes onto atlas coordinates in the atlas by a transformation that registers the corresponding image volume to the atlas. Furthermore, the nonmanually selecting step includes the step of computing a centroid of all the mapped atlas coordinates as an optimal target position of the deep brain stimulator in the atlas. Moreover, the nonmanually selecting step includes the step of projecting the optimal target position of the deep brain stimulator in the atlas onto the pre-operatively acquired image volume by an inverse of the transformation that registers the pre-operatively acquired image volume to the atlas so as to identify the initial optimal position of the deep brain stimulator in the targeted region of the brain of the living subject. The atlas in one embodiment is a common volume of reference in which the position of each deep brain stimulator can be recorded.

In one embodiment, the spatial coordinates of the deep brain stimulator are acquired intra-operatively by a positioning drive that translates physical coordinates of the deep brain stimulator into coordinates of the pre-operative image volume. In another embodiment, the spatial coordinates of the deep brain stimulator are acquired post-operatively by CT scans.

The nonrigid registration algorithm for registering a source image volume corresponding to one of the remaining N−1 image volumes to a target image volume corresponding to the atlas, in one embodiment, includes a demons algorithm that computes a transformation that minimizes the voxel-by-voxel intensity difference between the source image volume and the target image volume.

In another embodiment, the nonrigid registration algorithm registering a source image volume to a target image volume includes an adaptive base algorithm. The adaptive base algorithm includes the steps of defining a source image that corresponds to one of the remaining N−1 image volumes, defining a target image that corresponds to the atlas, and creating an image pyramid for each of the source image and the target image, respectively. Each image pyramid has M levels. Each level of the image pyramid has a resolution and is segmented with a corresponding scale so as to form a grid. Each image pyramid is formed such that level i of the pyramid has lower resolution and larger scale than level (i−1), where i=1, . . . , M, and M is an integer greater than 1. The adaptive base algorithm further includes the steps of defining a deformation field, $v(x)$, which registers the source image volume to the target image volume, and initializing the deformation field, $v(x)=v_M(x)$. Moreover, the adaptive base algorithm includes the step of computing the deformation field, $v_i(x)$, at level i of the image pyramids, where the deformation field $v_i(x)$ at level i is a sum of the deformation field at level (i+1) and a linear combination of a set of radial basis functions spaced on the grid of level i, so as to register the source image volume to the target image volume at level i and where the computing starts at level (M−1). Furthermore, the adaptive base algorithm includes the step of identifying regions of misregistration that is resulted from the computing step at level i. Moreover, the adaptive base algorithm includes the step of optimizing each of the regions of misregistration independently from each other by modifying the region of support and radial basis functions corresponding to the region in the deformation field $v_i(x)$. Additionally, the adaptive base algorithm includes the step of iterating the computing step, the identifying step and the optimal step at level (i−1) of the image pyramids till level 1 is reached so as to incrementally construct a final deformation field in the form of $$v(x)=v_1(x)+ \ldots +v_M(x).$$

The adaptive base algorithm further includes the step of optimizing a constraint scheme for enforcing a Jacobian matrix of the deformation field to remain uniformly invertible throughout a domain of the source image volume and a corresponding domain of the target image volume so as to generate topologically correct transformations between the source image volume and the target image volume.

In one embodiment, the step of finding a final position includes the steps of placing a microelectrode recording lead at the nonmanually selected initial optimal position, adjusting the position of the microelectrode recording lead from the initial optimal position so as to find a new position where resting firing frequencies are detected, replacing the microelectrode recording lead with an unipolar macrostimulation lead at the new position for delivering stimulation to the predetermined deep brain target, adjusting the position of the unipolar macrostimulation lead from the new position so as to find an adjusted position where optimal stimulation to the predetermined deep brain target is detected, and identifying the adjusted position as the final position in which the deep brain stimulator is to be placed.

In another aspect, the present invention relates to an apparatus of optimal placement of a deep brain stimulator in a targeted region of a brain of a living subject, where the deep brain stimulator includes a plurality of contact-electrodes. In one embodiment, the apparatus includes means for nonmanually selecting an initial optimal position in the targeted region, means for finding a final position from the initial optimal position, and means for placing the deep brain stimulator at the final position.

The means for nonmanually selecting an initial optimal position includes a controller that performs the step of choosing an image volume as a common volume of reference from a set of image volumes. The set of image volumes has N image volumes, and each is acquired pre-operatively from a brain of a living subject having a deep brain stimulator placed in a target, where N is an integer greater than 2. The controller further performs the steps of registering each of the remaining N−1 image volumes to the chosen common volume of reference by a nonrigid registration algorithm so as to create an atlas, and mapping spatial coordinates of the deep brain stimulator in each of the remaining N−1 image volumes onto atlas coordinates in the atlas by a transformation that registers the corresponding image volume to the atlas. Furthermore, the controller performs the step of computing a centroid of all the mapped atlas coordinates as an optimal target position of the deep brain stimulator in the atlas. Moreover, the controller further performs the step of projecting the optimal target position of the deep brain stimulator in the atlas onto the pre-operatively acquired image volume by an inverse of the transformation that registers the pre-operatively acquired image volume to the atlas so as to identify the initial optimal position of the deep brain stimulator in the targeted region of the brain of the living subject. In one embodiment, the atlas is a common volume of reference in which the position of each deep brain stimulator can be recorded. The controller includes a computer.

The spatial coordinates of the deep brain stimulator, in one embodiment, are acquired intra-operatively by a positioning drive that translates physical coordinates of the deep brain stimulator into coordinates of the pre-operative image volume. In another embodiment, the spatial coordinates of the deep brain stimulator are acquired post-operatively by CT scans.

In one embodiment, the nonrigid registration algorithm for registering a source image volume corresponding to one of the remaining N−1 image volumes to a target image volume corresponding to the atlas includes a demons algorithm that computes a transformation that minimizes the voxel-by-voxel intensity difference between the source image volume and the target image volume.

In another embodiment, the nonrigid registration algorithm registering a source image volume to a target image volume includes an adaptive base algorithm. The adaptive base algorithm includes the steps of defining a source image that corresponds to one of the remaining N−1 image volumes, defining a target image that corresponds to the atlas, and creating an image pyramid for each of the source image and the target image, respectively. Each image pyramid has M levels. Each level of the image pyramid has a resolution and is segmented with a corresponding scale so as to form a grid. Each image pyramid is formed such that level i of the pyramid has lower resolution and larger scale than level (i−1), where i=1, ..., M, and M is an integer greater than 1. The adaptive base algorithm further includes the steps of defining a deformation field, v(x), which registers the source image volume to the target image volume, and initializing the deformation field, $v(x)=v_M(x)$. Moreover, the adaptive base algorithm includes the step of computing the deformation field, $v_i(x)$, at level i of the image pyramids, where the deformation field $v_i(x)$ at level i is a sum of the deformation field at level (i+1) and a linear combination of a set of radial basis functions spaced on the grid of level i, so as to register the source image volume to the target image volume at level i and where the computing starts at level (M−1). Furthermore, the adaptive base algorithm includes the step of identifying regions of misregistration that is resulted from the computing step at level i. Moreover, the adaptive base algorithm includes the step of optimizing each of the regions of misregistration independently from each other by modifying the region of support and radial basis functions corresponding to the region in the deformation field $v_i(x)$. Additionally, the adaptive base algorithm includes the step of iterating the computing step, the identifying step and the optimal step at level (i−1) of the image pyramids till level 1 is reached so as to incrementally construct a final deformation field in the form of $$v(x)=v_1(x)+ \ldots +v_M(x).$$

The adaptive base algorithm further includes the step of optimizing a constraint scheme for enforcing a Jacobian matrix of the deformation field to remain uniformly invertible throughout a domain of the source image volume and a corresponding domain of the target image volume so as to generate topologically correct transformations between the source image volume and the target image volume.

The means for finding a final position in the targeted region includes a microelectrode recording lead placed at the nonmanually selected initial optimal position for finding a new position where resting firing frequencies are detected, an unipolar macrostimulation lead placed at the new position for finding the adjusted position where optimal stimulation to the predetermined deep brain target is detected, a platform for positioning the microelectrode recording lead and the unipolar macrostimulation into the corresponding positions, respectively, and a micropositioning drive attached to the platform for reading coordinates of positions of the microelectrode recording lead and the unipolar macrostimulation, respectively.

In yet another aspect, the present invention relates to a method for optimal placement of a deep brain stimulator in a targeted region of a brain of a living subject, where the deep brain stimulator includes a plurality of contact-electrodes. In one embodiment, the method has the step of nonmanually selecting an initial optimal position, which position is carried out pre-operatively. Furthermore the method includes the steps of finding a final position in the targeted region from the initial optimal position, and placing the deep brain stimulator at the final position, which are carried out intra-operatively.

In a further aspect, the present invention relates to an apparatus of optimal placement of a deep brain stimulator in a targeted region of a brain of a living subject, where the deep brain stimulator includes a plurality of contact-electrodes. In one embodiment, the apparatus includes a controller that performing the step of nonmanually selecting an initial optimal position. Furthermore, the controller performs the steps of finding a final position in the targeted region from the initial optimal position, and placing the deep brain stimulator at the final position.

These and other aspects of the present invention will become apparent from the following description of the preferred embodiment taken in conjunction with the following drawings, although variations and modifications therein may be affected without departing from the spirit and scope of the novel concepts of the disclosure.

DETAILED DESCRIPTION OF THE INVENTION

Figure 1:
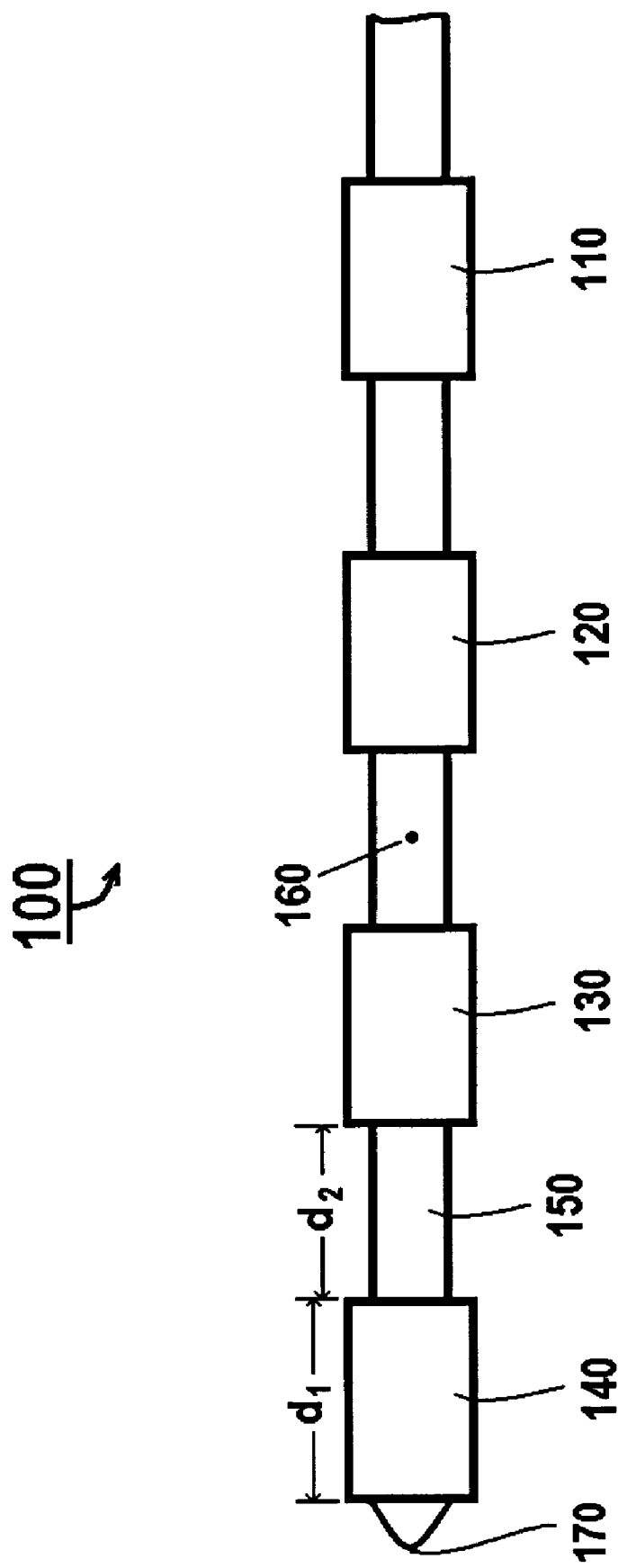
FIG. 1 schematically shows one example of a quadricpolar deep brain stimulator to be utilized to practice the present invention.

The present invention is more particularly described in the following examples that are intended as illustrative only since numerous modifications and variations therein will be apparent to those skilled in the art. Various embodiments of the invention are now described in detail. Referring to the drawings, like numbers indicate like parts throughout the views. As used in the description herein and throughout the claims that follow, the meaning of "a," "an," and "the" includes plural reference unless the context clearly dictates otherwise. Also, as used in the description herein and throughout the claims that follow, the meaning of "in" includes "in" and "on" unless the context clearly dictates otherwise. Additionally, some terms used in this specification are more specifically defined below.

Definitions

The terms used in this specification generally have their ordinary meanings in the art, within the context of the invention, and in the specific context where each term is used.

Certain terms that are used to describe the invention are discussed below, or elsewhere in the specification, to provide additional guidance to the practitioner in describing the apparatus and methods of the invention and how to make and use them. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only, and in no way limits the scope and meaning of the invention or of any exemplified term. Likewise, the invention is not limited to various embodiments given in this specification.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, the term "living subject" refers to a human being such as a patient, or an animal such as a lab testing monkey.

As used herein, "target" refers to an object of stimulation in a deep brain of a living subject for treatment of a brain-controlled disorder.

As used herein, "stimulation" refers to increase temporarily the activity of a body organ or part thereof responsive to an input signal to the body organ or part.

The term "project," or "map," or "transform," as used herein, is synonym in the specification and refers to a transformation of a point from a source image volume to a target image volume, and vice versa.

The term "place," or "implant," or "insert," as used herein, is synonym in the specification and refers to put or embed a device, such as a microelectrode recording lead, macrostimulation lead, and/or a deep brain stimulator, into a target region of the body of a living subject.

Overview of the Invention

Optimal placement of a deep brain stimulator (DBS) according to the present invention, among other things, comprises an iterative procedure and associated means for performing the task. A target is chosen pre-operatively based on anatomical landmarks identified on MR images. This target point is used as an initial position that is refined intra-operatively using information at least from one of microelectrode recordings and macrostimulation. Because the length of the procedure increases with the time it takes to adjust the DBS to its final position, a good initial position is critical. In the present invention, a method for optimal placement of a deep brain stimulator in a targeted region of a brain of a living subject for optimal deep brain stimulation is invented, which includes the step of automatically or nonmanually selecting an initial optimal position by using an atlas and non-rigid registration algorithms. Comparisons the automatically selected initial optimal position and the initial position selected by a neurosurgeon with the final position of the DBS for eight subthalamic nucleus (STN) patients show that the automatically selected initial optimal positions are closer to the final positions of the DBS than the initial positions selected manually.

The method further includes the steps of refining the nonmanually selected initial optimal position to determine the final position and placing the deep brain stimulator at the final position in the targeted region of the brain of the living subject.

In one embodiment, nonmanually selecting the initial optimal position includes the following steps: at first, an image volume is chosen as a common volume of reference from a set of image volumes. The set of image volumes has N image volumes, and each is acquired from a brain of a patent having a deep brain stimulator placed in a target, such as subthalamic nucleus (STN), where N is an integer greater than 2. Second, each of the remaining N–1 image volumes is registered to the chosen common volume of reference by a nonrigid registration algorithm so as to create an atlas. Then, spatial coordinates of the deep brain stimulator in each of the remaining N–1 image volumes are mapped onto atlas coordinates in the atlas by a transformation that registers the corresponding image volume to the atlas. Furthermore, a centroid of all the mapped atlas coordinates is computed as an optimal target position of the deep brain stimulator in the atlas. Moreover, the optimal target position of the deep brain stimulator in the atlas is projected onto the pre-operatively acquired image volume by an inverse of the transformation that registers the pre-operatively acquired mage volume to the atlas so as to identify the initial optimal position of the deep brain stimulator in the targeted region of the brain of the living subject.

In one embodiment, the step of refining the nonmanually selected initial optimal position includes the following steps: (a), a microelectrode recording lead is placed at the nonmanually selected initial optimal position, (b), the position of the microelectrode recording lead is adjusted so as to find a new position where resting firing frequencies are detected, (c) the microelectrode recording lead is replaced with an unipolar macrostimulation lead at the new position for delivering stimulation to the predetermined deep brain target, (d) the position of the unipolar macrostimulation lead is adjusted so as to find an adjusted position where optimal stimulation to the predetermined deep brain target is detected, and (e) the adjusted position is identified as the final position in which the deep brain stimulator is to be placed.

Methods and Implementations

Patients and Pre-Operative Target Selection

In one embodiment of the present invention, a group of 8 patients who undergo deep brain stimulator implantation at a target of the subthalamic nucleus (STN) is chosen to gather a set of data for evaluating the invented method. Each patient, or a living subject of study, was assigned a number from S1 to S8 as his or her identification. The data was collected after obtaining an Independent Research Board (IRB) approval at Vanderbilt University (Vanderbilt University IRB# 01-0809).

All patients undergoing consideration for this DBS implantation at the target of the STN are first evaluated by a neurologist specializing in movement disorders, and their medications are adjusted to optimize their condition. If patients reach advanced Parkinsonian symptoms, such as rigidity, bradykinesia, tremor, and dyskinesia, despite optimal medical therapy, they are considered for the surgical therapy by a multi-disciplinary group involving neurology, neurosurgery, neurophysiology, and neuropsychiatry specialists. Target selection is decided upon by the team if no contraindications exist. A majority of patients with the above symptoms are recommended for STN targeting of DBS therapy. Pre-operative target identification is performed by the functional neurosurgeon (PEK) and is based on an identification of the AC-PC location seen on MRI (3D SPGR volumes, TR: 12.2 msec, TE: 2.4 msec, voxel dimensions $0.85 \times 0.85 \times 1.3$ mm$^3$) pre-operatively. For the STN target, a preliminary point is chosen at 4 mm posterior, 12 mm lateral, and 4 mm inferior to the mid-commissural point. The adjustments for the initial intended target are made based on the width of the third ventricle and anatomical asymmetries noted on the MRI scan, but these adjustments usually have less than 1 mm deviations from the initial intended target location.

Guidance System and Intra-Operative Placement

Traditional methodology for carrying out this stepwise target localization and implantation procedure has been based on an externally fixed, rigid fixture, called a stereotactic frame that encompasses the patient's head and upon which the micro-manipulating equipment can be mounted and maneuvered with sub-millimetric precision. These various stereotactic frames have been optimized to obtain accurate images used to create the initial target trajectory and plan and then to reduce erroneous movement associated with passage of the test electrodes and the final implantation [5]. These frames typically require mounting the day of surgery, subsequent imaging with either CT and/or MRI axial slices, and target planning prior to starting the actual procedure of intra-operative mapping and ultimate placement of the electrode implantation into the final target.

Figure 2B:
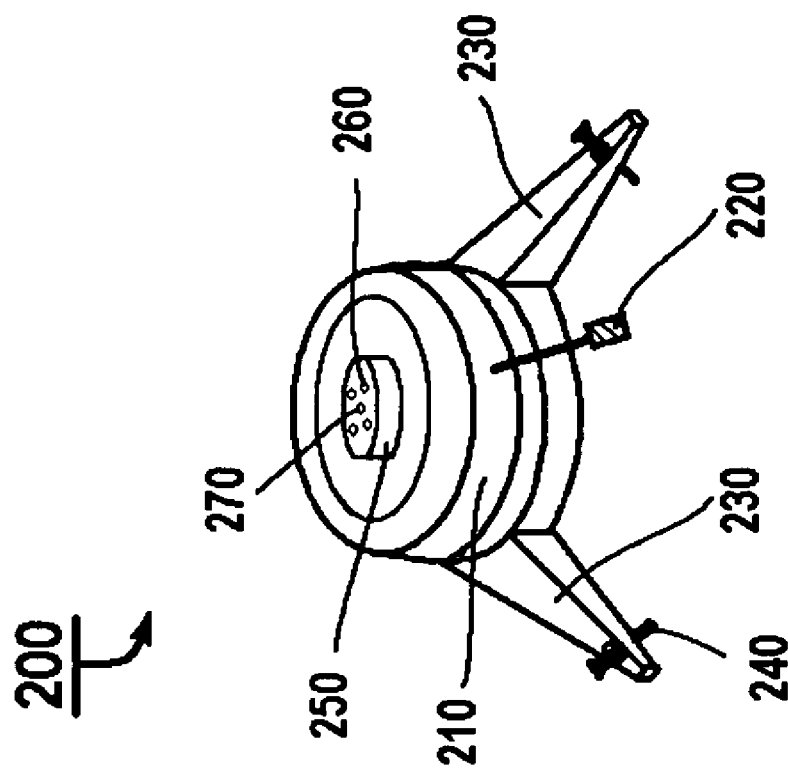
FIG. 2 schematically shows a platform to be utilized to practice the present invention: (a) a perspective view of the platform, and (b) a perspective view of the platform with a guiding member in place.
Figure 2A:
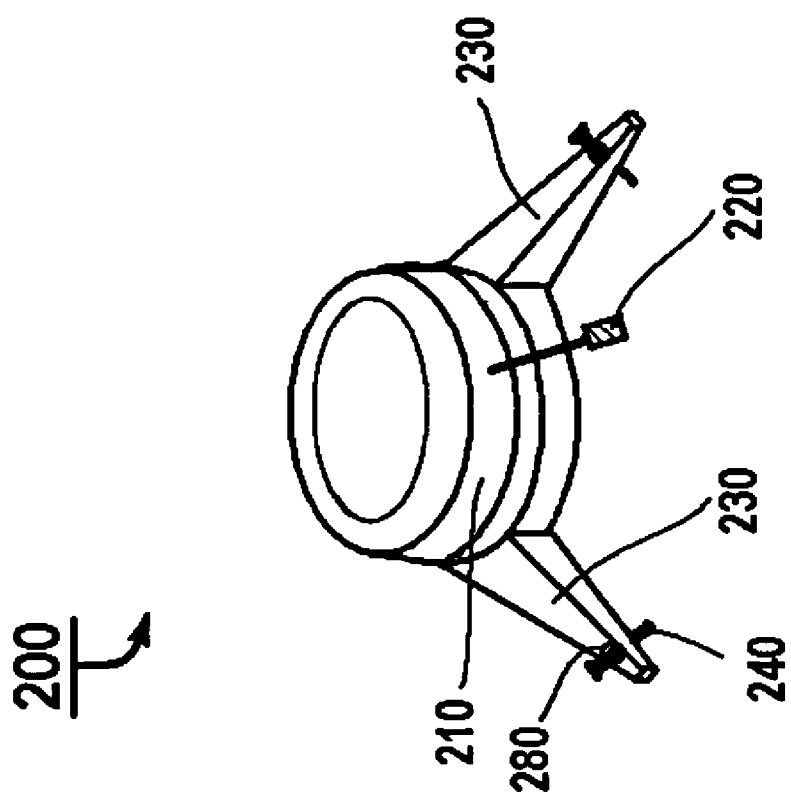

Recently, a FDA approved miniature stereotactic frame, called a Starfix platform (microTargeting®, FHC Corporation; Bowdoinham, Me.), has become clinically available. This device, also referred as a platform hereafter, allows for more versatility with elective stereotactic procedures, such as DBS implantation. Referring to FIGS. 2A and 2B, the platform 200 has a platform body 210, an adjustor 220 attached to the platform body 210 and a plurality of legs 230 outwardly and equal-angularly extending from the platform body 210. Each of the plurality of legs 230 has a hole 280 at an end portion for receiving a corresponding fiducial marker post 240 implanted into the outer table of the skull of a patient so as to secure the platform 210. The platform 210 also has a guiding member 250. The guiding member 250 has a plurality of guiding tubes 260 including a center guiding tube 270. The positions of the guiding tubes 260 including the central tube 270 can be adjusted by the adjustor 220. The platform 210 is currently manufactured as a customized tripod that can be mounted onto bone-based fiducial marker posts 240. Each platform is uniquely manufactured based on a stereotactically planned trajectory using software designed to mathematically relate the location of such bone markers with respect to brain structures [6]. The bone-based fiducial markers having a fluid-filled cylinder that is visible on both CT and MR images is detachably attached to a post that is implanted into the outer table of the skull. These images can then be used in the stereotactic software to designate a trajectory in relation to the bone-based marker posts. The plan is sent to the manufacturer who then translates the stereotactic plan into a customized platform for a given trajectory through a rapid prototyping facility. The resultant platform is shipped to the hospital within a certain time frame and is used for mounting the same types of micromanipulators that are used on traditional stereotactic frames. The remaining portion of the procedure is the same with respect to intra-operative localization of the final target of implantation with the patient awake.

Each patient undergoing surgery receives either one (for unilateral DBS implantation) or two (for bilateral DBS implantation) platforms. Each leg of the platform is attached to a corresponding bone-implanted post. For each patient, the acquisition of data proceeds in three stages. First, under anesthesia, the fiducial marker posts are implanted onto predetermined positions on the skull of the patient, Acustar™ (Z-Kat, Inc., Hollywood, Fla.) fiducial markers are attached to the posts. The use of this marker and post in open craniotomies has been reported on earlier [6]. Other fiducial markers and posts can also be used to practice the present invention. CT and MR image volumes are acquired with the patient anesthetized and head taped to the table to minimize motion. For examples, CT images acquired at kvp=120 V, exposure=350 mas, 512×512 pixels ranging in size from 0.49 to 0.62 mm, slice thickness=2 mm for one patient, 1.3 mm for 2 patients, 1 mm for all others. MR images are 3D SPGR volumes, TR: 12.2, TE: 2.4, voxel dimensions 0.85×0.85×1.3 mm$^3$ except for subject S7 for which the voxel dimensions are 1×1×1.3 mm$^3$. After image acquisition, the fiducial markers are removed. With the help of MR-CT registration software, for instance, VoXim® (FHC Corporation, Bowdoinham, Me.), the surgeon selects the initial target points based on AC-PC coordinates and associated entry points on the surface of the skull. In addition, the centroids of the markers and the directions of their posts are determined from the acquired images. These data are sent electronically to a fabrication plant where a customized platform is manufactured to fit the posts and provide an opening positioned over the entry point and oriented toward the target.

Figure 3:
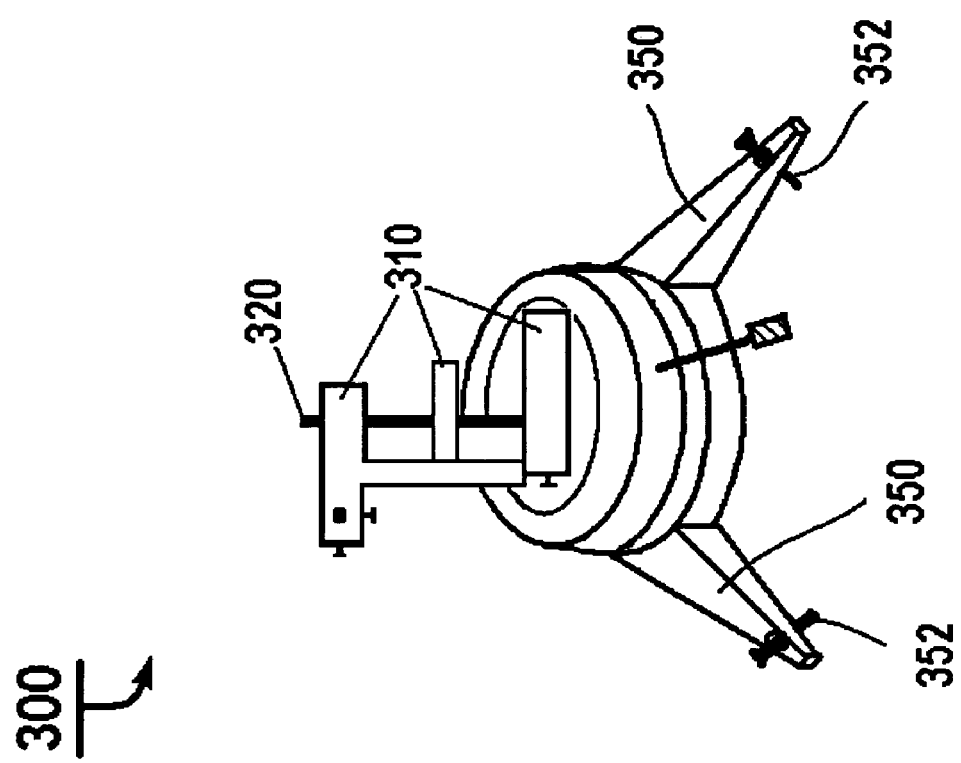
FIG. 3 schematically shows a system to be utilized to practice the present invention.

Second, surgery begins with the drilling of a burr hole, for instance, have 14 mm in diameter. Referring to FIG. 3, an adaptor (not shown here) is attached to each post 352, the platform 350 is attached to the adaptors, and a micropositioning drive 310 is attached to the platform 350. In one embodiment, microTargeting® (FHC Corporation, Bowdoinham, Me.) is employed as the micropositioning drive. A microelectrode recording lead is placed into the patient at the selected initial target position through the central tube of the guide member attached to the platform. The position of the microelectrode recording lead, thus the selected initial target position, is adjusted so that resting firing frequencies are noted or detected. The adjustment involves three-dimensional adjustment. In addition to changes in depth, it is possible to re-insert a probe 320 along parallel tracks distributed within a 10 mm circle around the initial track. The microelectrode lead is removed and a unipolar macrostimulation lead is inserted to the adjusted position as determined by the microelectrode recordings. With the patient awake, response to stimulation generated from the macrostimulation lead is monitored as the position of the macrostimulation lead is further adjusted until optimal stimulation to the deep brain target is detected. When the final positions are selected, the macrostimulation lead is removed and a deep brain stimulator lead is inserted at the final position. In one embodiment, the DBS lead includes at least one of Medtronic #3387 and #3389 *quadripolar lead®* (Medtronic, Inc., Minneapolis, Minn.), as shown in FIG. 1 as described supra. Other types of DBS lead can also be utilized to practice the present invention. The lead is inserted to a deep such that the centroid 160 of the four electrodes 110–140 of the DBS lead 100 is coincident with the final position of the electrode on the unipolar macrostimulation lead. The proximal end of the DBS lead is then anchored to the skull and buried beneath the scalp. The platform is then removed. Within twenty-four hours of surgery, the imaging markers are re-attached to the posts and a post-operative CT scan is acquired. If no complications occur, the patient is discharged home within a day of the surgery. During the entire procedure coordinates are read on the mircodrive. These physical coordinates can be transformed into pre-operative CT coordinates using the software used for pre-operative planning.

Third, within about two weeks the patient is brought back to the operating room and the DBS lead is attached to an internal pulse generator, for example, Soletra (Medtronic, Inc., Minneapolis, Minn.), under general anesthesia. This is usually done as an outpatient procedure. Programming of the generators is performed typically as an outpatient one month later by a neurologist.

Figure 4:
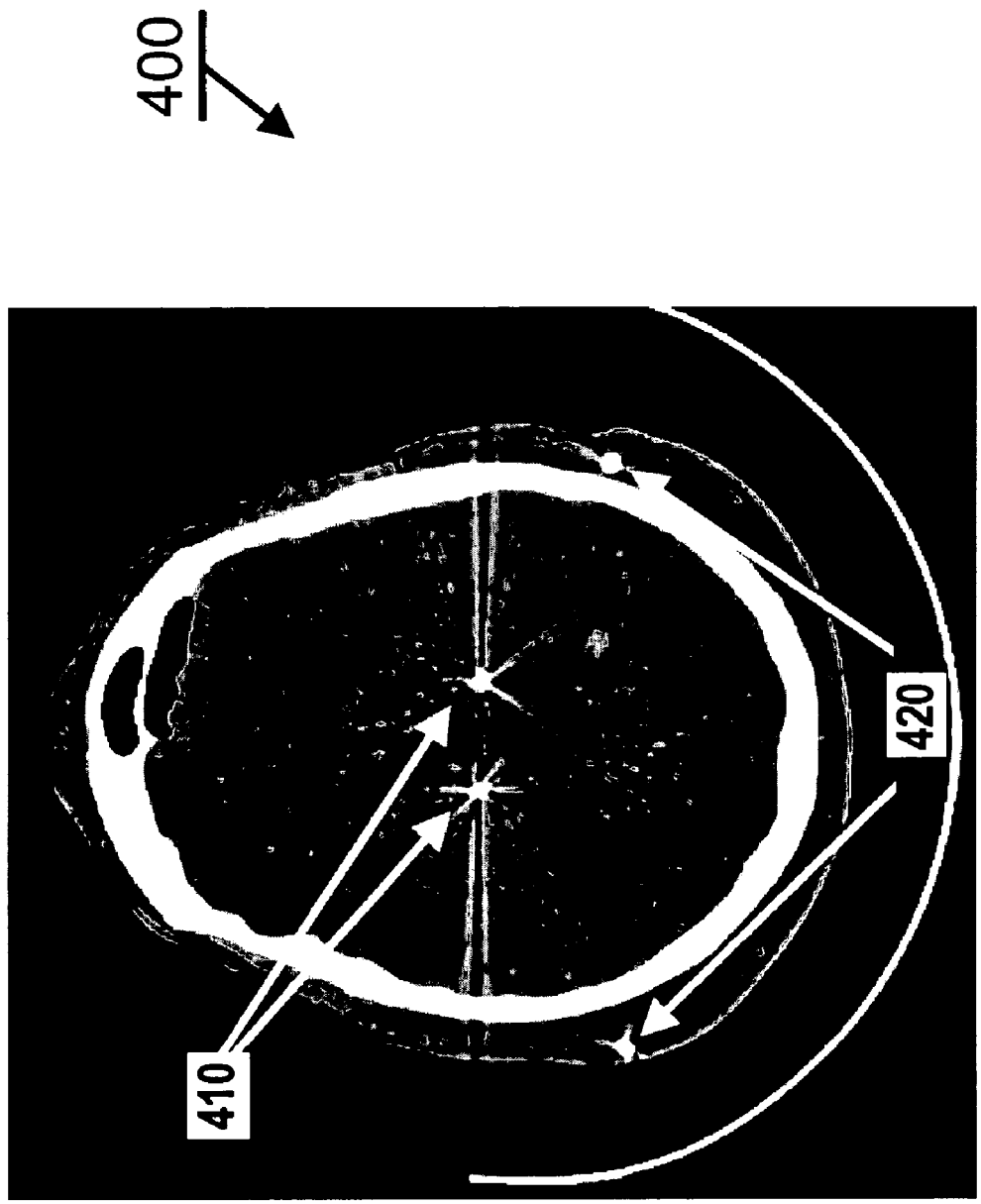
FIG. 4 shows a post-operative CT image of a patient after the bilateral DBS implantation according to one embodiment of the present invention.

To assess the final position of the DBS in the post-operative CT scans, the centroid of the DBS contact-electrodes needs to be detected in the CT images. Referring back to FIG. 1, the DBS lead 100 includes four exposed platinum/iridium contact-electrodes 110, 120, 130 and 140. The centroid 160 of the DBS contact-electrodes is at midway between the inner two contact-electrodes 120 and 130, which is the target point to which the surgeon attempts to deliver stimulation. Referring to FIG. 4, a post-operative CT image 400 of a patient after the bilateral DBS implantation having two DBS leads 410 is shown. The wire leads 420 are running under skin from the DBS leads 410 to the internal pulse generator.

Atlas Creation and Prediction of an Optimal Target Position

The atlas is a common frame of reference in which the position of each individual DBS can be recorded. Creation of the atlas requires registering individual image volumes to a common reference volume, which corresponds to the spatial normalization of each individual brain image. Two nonrigid registration algorithms developed at Vanderbilt University are utilized hereto. Other algorithms may also be utilized to practice the present invention.

The first one is called a demon algorithm proposed by Thirion [8]. The demons algorithm computes a transformation that minimizes the voxel-by-voxel intensity difference between the source image volume and the target image volume. This method is itself derived from the instantaneous optical flow equation proposed by Horn and Schunck [20] for motion tracking in image sequences (in the present invention, the two image volumes to be registered are viewed as two frames in a sequence). The basic assumption on which this equation is based is that the image intensity value of a point in the anatomy does not change as it is displaced. This permits the computation of a velocity vector (or in the invention a displacement vector) at each voxel that obeys the following equation:

$$\frac{\partial i}{\partial x}\frac{\partial x}{\partial t} + \frac{\partial i}{\partial y}\frac{\partial y}{\partial t} + \frac{\partial i}{\partial z}\frac{\partial z}{\partial t} = -\frac{\partial i}{\partial t}$$

in which i is the intensity value in the image at the point with coordinates (x, y, z). This equation is under-constrained and regularization techniques are used to smooth the displacement field. Thirion proposes to decouple the computation of the displacement field and its regularization as opposed to casting the problem as one single optimization problem. The displacement at each point in the image is first computed by solving the equation. The displacement field is then regularized by filtering it with a Gaussian filter. The larger the standard deviation of this filter is, the smoother the displacement field is. The algorithm is iteratively applied in a multi-scale way. The matching is first computed on coarse downsampled images then successively to images with a finer spatial resolution. This strategy has several advantages: it speeds up the computations, improves the convergence properties of the algorithm, and uses the fact that, for human anatomy, macroscopic features are, in general, more stable than microscopic features. In one embodiment of the present invention, two image pyramids are derived from the images to be registered, up to a predetermined scale. A number of iterations of the algorithm are applied to the images at the coarsest scale and the results obtained at this scale serve as initial conditions for the next one until the finer scale is reached. Furthermore, an additional mechanism that calls the bijectivity constraint is used to ensure a one-to-one correspondence between the two images to be matched. Following the approach proposed by Burr [21] this is done by computing both a direct and a reverse deformation field which are maintained compatible such that $T_{1 \rightarrow 2} T_{2 \rightarrow 1} \cong I$, with $T_{1 \rightarrow 2}$ the deformation field from image 1 to image 2, $T_{2 \rightarrow 1}$ the deformation field from image 2 to image 1, indicating composition, and I the identity transformation. This greatly increases the robustness of the algorithm, and it has the advantage of insuring that both the forward, i.e, from the reference volume to the individual volumes, and reverse, i.e., from the individual volumes to the reference volumes, transformations are one-to-one.

In one embodiment of the present invention, another non-rigid algorithm called an Adaptive Basis Algorithm (ABA) [9] is developed, which operates on a quite different principle. Rather than trying to minimize the intensity differences at every voxel, this algorithm computes a transformation that maximizes the Mutual Information (MI) between the images. In this technique, inspired by the work of Rueckert et al. [10] and Meyer et al [11], the deformation that registers one image (a source image) onto the other (a target image) is modeled with a linear combination of radial basis functions with finite support. The similarity measure that drives the registration process is the mutual information between the source image and the target image. In this algorithm, several improvements over existing mutual information-based non-rigid registration algorithm are implemented. These include working on an irregular grid, adapting the compliance of the transformation locally, decoupling a very large optimization problem into several smaller ones, and deriving schemes to guarantee the topological correctness of the transformations. Specifically, the adaptive base algorithm includes the following steps: at first, a source image and a target image are defined to be one of the remaining N−1 image volumes and the atlas, respectively. Second, an image pyramid for each of the source image and the target image is created, respectively. Each image pyramid has M levels. Each level of the image pyramid has a resolution and is segmented with a corresponding scale so as to form a grid. Each image pyramid is formed such that level i of the pyramid has lower resolution and larger scale than level (i−1), where i=1, . . . , M, and M is an integer greater than 1. Then, a deformation field, v(x), which registers the source image volume to the target image volume, is defined, and the deformation field is further initialized as $v(x)=v_M(x)$. In one embodiment, the deformation field is initially set to be zero. Furthermore, the deformation field, $v_i(x)$, is computed at level i of the image pyramids, where the deformation field $v_i(x)$ at level i is a sum of the deformation field at level (i+1) and a linear combination of a set of radial basis functions spaced on the grid of level i, so as to register the source image volume to the target image volume at level i and where the computing starts at level (M−1). Moreover, regions of misregistration are identified, which is resulted from the step of computing the deformation field $v_i(x)$ at level i. Additionally each of the regions of misregistration are optimized independently from each other by modifying the region of support and radial basis functions corresponding to the region in the deformation field $v_i(x)$. Furthermore, the computing step, the identifying step and the optimal step are iterated at level (i−1) of the image pyramids till level 1 is reached so as to incrementally construct a final deformation field in the form of $$v(x) = v_1(x) + \ldots + v_M(x).$$

The adaptive base algorithm further includes the step of optimizing a constraint scheme for enforcing a Jacobian matrix of the deformation field to remain uniformly invertible throughout a domain of the source image volume and a corresponding domain of the target image volume so as to generate topologically correct transformations between the source image volume and the target image volume.

To create an atlas, a MR image volume is empirically chosen as a common volume of reference from a set of MR image volumes. The set of image volumes has N image volumes, and each is pre-acquired from a brain of a living subject. In this study, the set of image volumes were acquired from a group of 8 patients. Each of the remaining N−1 image volumes is registered to the chosen common volume of reference by the nonrigid registration algorithm (the demon algorithm and/or the ABA algorithm) as to create an atlas. Once the transformation between one image volume and the atlas is computed, the spatial coordinates of the DBS in this volume can be transformed into atlas coordinates. The optimal DBS position in the atlas is computed as the centroid of all the DBS positions after their projection onto the atlas.

Predicting the initial optimal DBS position for each patient is the inverse of the operation described above. It includes projecting the optimal DBS position from the atlas to each individual image volume. This does not require another registration step because the transformation from the patient to the atlas and from the atlas to the patient are computed simultaneously. The nonrigid registration algorithms impose constraints on these transformations to keep them almost inverse of each other to produce bijective transformations. For instance, to predict an initial optimal position in an image volume of a patent that the deep brain stimulator is to be implanted using the atlas and nonrigid registration algorithm, the image volume of the patent needs being registered to the atlas by the nonrigid registration algorithm so as to find a registration transformation of the image volume to the atlas. Application of an inverse of the transformation will project the optimal target position of the deep brain stimulator in the atlas to the image volume so as to identify the initial optimal position of the deep brain stimulator in the targeted region of the brain of the patient.

Because the intra-operative coordinates are given in terms of pre-operative CT coordinates, while the non-rigid registration algorithms need to be applied on MR images, an additional step of registering the MR and CT images is required. Corresponding MR and CT image volumes are registered using a rigid body transformation also computed using mutual information as proposed by Maes et al. [12].

Visual Evaluation of the Registration Results

Two examples of obtaining the DBS coordinates according to the present invention are presented. The first, called intra-operative, relies on coordinates provided by a STarFix guidance system (FHC Corporation; Bowdoinham, Me.) during surgery. This system translates the physical coordinates of the DBS electrode into pre-operative CT coordinates. The second, called post-operative CT, relies on an algorithm to get the centroid of the deep brain stimulator in the post-operative CT scans [22]. One can expect differences between these coordinates, the causes of which are several. First, the STarFix system is not perfectly accurate. Second, the intra-operative target point is arrived at with a microstimulating electrode. This electrode is then replaced by the permanent DBS stimulator, which introduces the surgical placement error. Third, the brain may shift during surgery because of swelling and/or loss of cerebrospinal fluid (CSF). After surgery, the brain returns to its normal state, which also causes the electrode to move.

Figure 5:
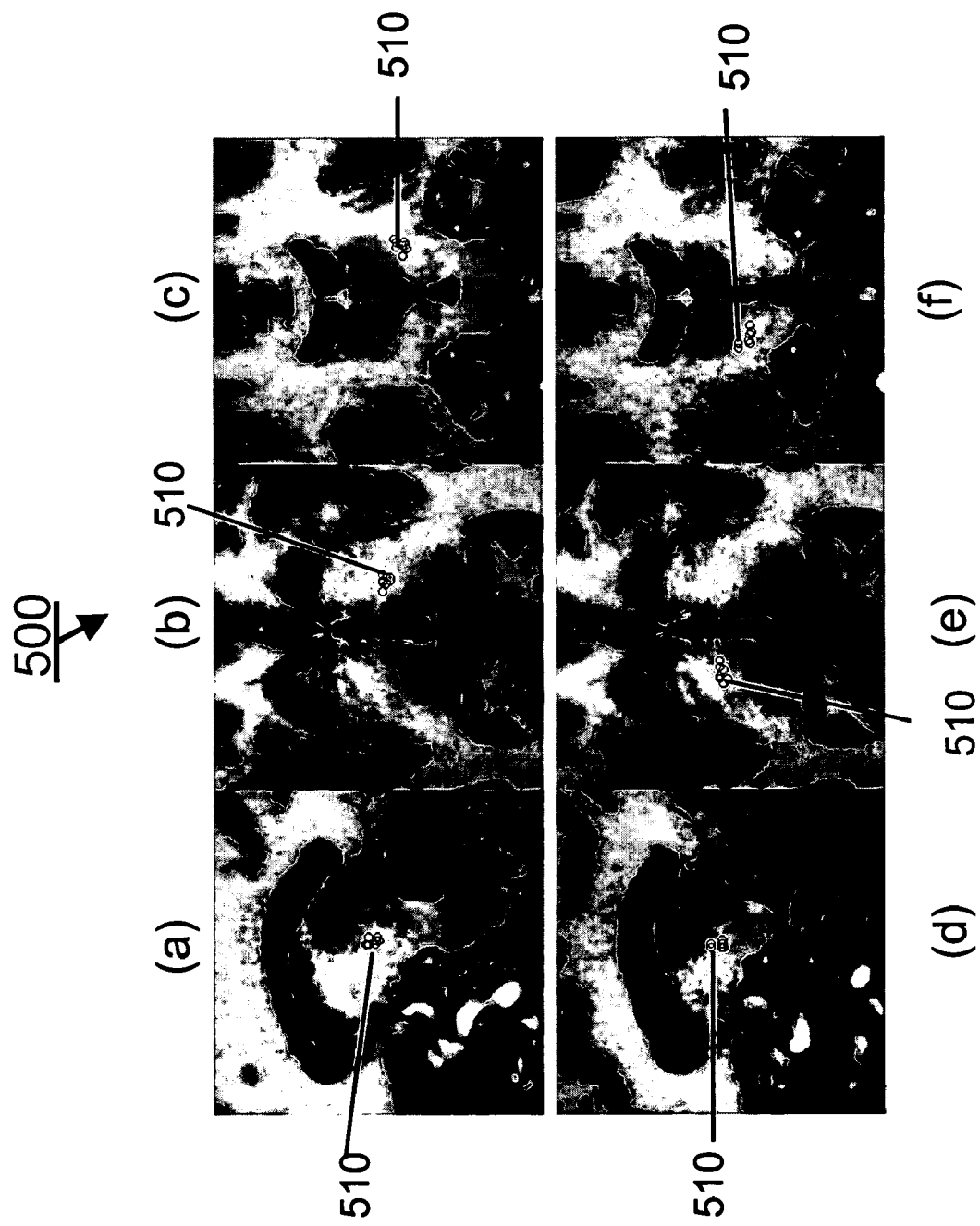
FIG. 5 shows an atlas and atlas coordinates transformed from the final DBS positions acquired intra-operatively according to one embodiment of the present invention: (a) a sagital view of the atlas for the lift side STN targets, (b) a transverse view of the atlas for the lift side STN targets, (c) a coronal view of the atlas for the lift side STN targets, (d) a sagital view of the atlas for the right side STN targets, (e) a transverse view of the atlas for the right side STN targets, and (f) a coronal view of the atlas for the right side STN targets.
Figure 6:
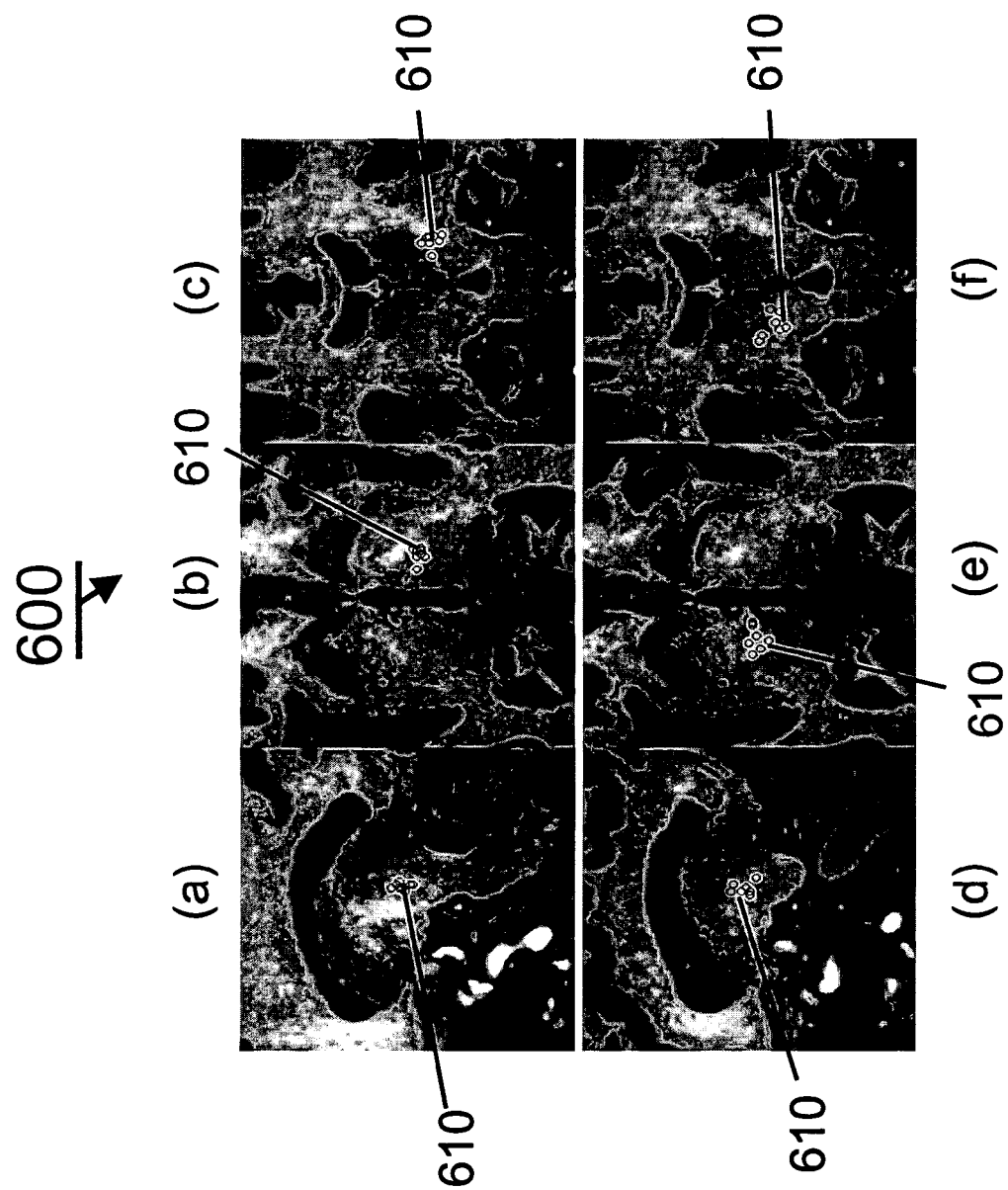
FIG. 6 shows an atlas and atlas coordinates transformed from the final DBS positions acquired post-operatively according to one embodiment of the present invention: (a) a sagital view of the atlas for the lift side STN targets, (b) a transverse view of the atlas for the lift side STN targets, (c) a coronal view of the atlas for the lift side STN targets, (d) a sagital view of the atlas for the right side STN targets, (e) a transverse view of the atlas for the right side STN targets, and (f) a coronal view of the atlas for the right side STN targets.

Referring now to FIGS. 5 and 6, first to FIG. 5, each circle 510 corresponds to an atlas position of a final DBS target projected onto the atlas 500. The final DBS target is acquired intra-operatively by a STarFix guidance system (FHC Corporation; Bowdoinham, Me.). FIGS. 5(a) and 5(d), 5(b) and 5(e), and 5(c) and 5(f) respectively show a sagital, transverse, and coronal view of the atlas passing through the centroid of atlas coordinates of the DBS targets. FIGS. 5(a)–5(c) are for the case of which the final DBS targets are on the left side STN, while FIGS. 5(d)–5(f) on the right side STN. The results are obtained with the ABA algorithm. The results are qualitatively similar with the demons algorithm. In FIG. 5, spatial coordinates of the individual stimulators have been acquired intra-operatively by a STarFix guidance system. FIG. 6 represents the same information as FIG. 5, except the spatial coordinates of the DBS targets are acquired with post-operative CT scans. In FIG. 6, each circle 610 corresponds to the atlas position of a final DBS target projected onto the atlas 600.

FIGS. 5 and 6 show that the atlas coordinates 510 projected from the spatial coordinates of the DBS positions acquired intra-operatively form a tight cluster than that of the atlas coordinates 610 projected from the spatial coordinates of the DBS positions acquired post-operatively form.

Projection of the Final DBS Positions onto the Atlas

Table 1 shows the atlas coordinates transformed from the spatial coordinates of the final DBS positions for the eight bilateral STN patients by using the ABA algorithms. The DBS coordinates are acquired intra-operatively. Each patient, or a living subject of study, is assigned a number from S1 to S8 in column Subject as his or her identification. Columns Left and Right represent locations of the bilateral DBS, that is, column Left corresponds to the left side implantation of the DBS, while column Right corresponds to the right side implantation of the DBS. Sub-columns X, Y and Z are atlas coordinates of a DBS placed in a specific target region (left side or right side) for a specific patient, which corresponds to an individual point in the atlas, represented by a corresponding circle 510 in FIG. 5. Rows S1–S8 represent a set of atlas coordinates of a bilateral DBS of patient S1–S8, respectively. For instance, the $6^{th}$ row of Table 1 represents patient S3 having a bilateral DBS implantation, where the atlas coordinates of the left side DBS is (X, Y, Z)=(122.47, 106.30, 53.44) mm, and the atlas coordinates of the left side DBS is (X, Y, Z)=(96.86, 107.02, 50.24) mm. The centroid of the atlas coordinates of the DBS positions of the eight bilateral STN patients is computed for the left side implantation and the right side implantation, respectively, which are presented in Row Mean. Row STD represents a standard deviation the atlas coordinates relative to the centriod. Row SEM is a standard error of the mean. The Euclidean distance between each point in the atlas and its corresponding centroid is represented in the Dc column.

TABLE 1

Atlas coordinates transformed from spatial coordinates of the final DBS positions that are acquired intra-operatively using the ABA algorithms.
Atlas Coordinates Transformed by the Adaptive Basis Algorithm (in unit of mm)

| Sub-ject | Left | | | | Right | | | |
|---|---|---|---|---|---|---|---|---|
| | X | Y | Z | Dc | X | Y | Z | Dc |
| S1 | 124.28 | 106.39 | 53.98 | 2.58 | 95.47 | 106.20 | 53.20 | 3.52 |
| S2 | 121.88 | 106.30 | 53.44 | 1.44 | | | | |
| S3 | 122.47 | 107.80 | 51.18 | 1.43 | 96.86 | 107.02 | 50.24 | 2.12 |
| S4 | 119.79 | 106.27 | 51.78 | 2.74 | 101.38 | 104.91 | 50.23 | 3.40 |
| S5 | 123.42 | 107.41 | 51.40 | 1.42 | 99.10 | 105.99 | 50.19 | 1.35 |
| S6 | 123.42 | 107.99 | 53.21 | 1.82 | 96.68 | 104.69 | 52.96 | 2.57 |
| S7 | 122.48 | 105.80 | 51.90 | 1.07 | 97.54 | 104.98 | 50.51 | 0.92 |
| S8 | 121.70 | 106.60 | 50.91 | 1.52 | 99.85 | 104.69 | 49.63 | 2.34 |
| Mean | 122.43 | 106.82 | 52.22 | 1.75 | 98.12 | 105.49 | 51.00 | 2.32 |
| STD | 1.37 | 0.81 | 1.16 | 0.60 | 2.07 | 0.91 | 1.45 | 0.97 |
| SEM | 0.49 | 0.28 | 0.41 | 0.21 | 0.73 | 0.32 | 0.51 | 0.34 |

Similar to Table 1, Table 2 shows the atlas coordinates transformed from the spatial coordinates of the final DBS positions for the eight bilateral STN patients by using the demons algorithms. The DBS coordinates are acquired intra-operatively.

Tables 1 and 2 have shown that the distance between the left side centroids computed with the ABA algorithm and the demons algorithm is 1.22 mm, and the distance between the right side centroids computed with the ABA algorithm and the demons algorithm is 1.16 mm.

The small values of the mean value, standard deviation (STD), and standard error of the mean (SEM) results show that the final positions of the DBSs transformed into atlas coordinates result in tight clusters. It is also worth noting that even though these two algorithms are based on very different similarity measures, they lead to essentially identical results, suggesting that the accuracy-limiting factor is not the registration algorithm used but either the spatial resolution of the MR images, the accuracy of the DBS positioning system, a bias introduced by the spatial normalization scheme, normal inter-subject variation, suboptimal intra-operative selection of the target, or a combination of these.

TABLE 2

Atlas coordinates transformed from spatial coordinates of the final DBS positions that are acquired intra-operatively using the demons algorithm.
Atlas Coordinates Transformed by the Demons Algorithm (in unit of mm)

| Subject | Left | | | | Right | | | |
|---|---|---|---|---|---|---|---|---|
| | X | Y | Z | Dc | X | Y | Z | Dc |
| S1 | 124.28 | 106.39 | 53.98 | 2.29 | 95.47 | 106.20 | 53.20 | 2.90 |
| S2 | 121.60 | 104.24 | 54.43 | 1.94 | | | | |
| S3 | 122.03 | 106.52 | 53.04 | 0.88 | 95.92 | 105.95 | 51.87 | 2.14 |
| S4 | 120.31 | 106.73 | 51.97 | 2.54 | 99.78 | 105.72 | 51.23 | 2.21 |
| S5 | 123.11 | 106.00 | 52.77 | 1.08 | 98.85 | 104.68 | 51.94 | 1.08 |
| S6 | 122.42 | 105.63 | 54.60 | 1.32 | 97.01 | 103.79 | 53.97 | 2.44 |
| S7 | 121.86 | 104.44 | 53.44 | 1.32 | 97.89 | 104.19 | 52.34 | 0.89 |
| S8 | 122.07 | 105.63 | 52.16 | 1.15 | 99.92 | 104.58 | 49.61 | 3.22 |
| Mean | 122.21 | 105.70 | 53.30 | 1.56 | 97.83 | 105.01 | 52.02 | 2.12 |
| STD | 1.15 | 0.93 | 0.99 | 0.61 | 1.78 | 0.94 | 1.40 | 0.87 |
| SEM | 0.41 | 0.33 | 0.35 | 0.22 | 0.63 | 0.33 | 0.5 | 0.31 |

Tables 3 and 4 show the same information as Tables 2 and 3 but spatial coordinates of the deep brain stimulators are acquired from the post-operative CT scans. A comparison of Tables 1 and 2 with Tables 3 and 4 shows clearly that atlas coordinates of the DBS positions do not cluster as well when the coordinates are acquired post-operatively as when the coordinates are acquired intra-operatively. The results are also shown in FIGS. 5 and 6, where the spatial coordinates of the DBS positions are acquired intra-operatively in FIG. 5, consequently, the projected atlas coordinates 510 of the DBS positions form a tight cluster, while in FIG. 6, the spatial coordinates of the DBS positions are acquired post-operatively, as a result, the projected atlas coordinates 610 of the DBS positions form a cluster looser than what the atlas coordinates 510 form.

The distance between an individual atlas point projected from a corresponding DBS position and the centroid of atlas coordinates projected from DBS positions of eight patients is significantly smaller for the intra-operative coordinates than that for the post-operative CT coordinates. Statistical significances for one-sided t-tests are as follows: ABA algorithm for a left side STN target ($P<0.03$), Demons algorithm for a left side STN target ($P<0.01$), ABA algorithm for a right side STN target ($P<0.01$), Demons algorithm for a right side STN target ($P<0.01$).

TABLE 3

Atlas coordinates transformed from spatial coordinates of the final DBS positions that are acquired with postoperative CT scans using the ABA algorithm.
Atlas Coordinates Transformed by the Adaptive Basis Algorithm (in unit of mm)

| Sub-ject | Left | | | | Right | | | |
|---|---|---|---|---|---|---|---|---|
| | X | Y | Z | Dc | X | Y | Z | Dc |
| S1 | 123.01 | 107.65 | 53.81 | 1.69 | 95.38 | 107.6 | 54.73 | 4.11 |
| S2 | 121.44 | 107.14 | 55.25 | 2.87 | | | | |
| S3 | 123.88 | 108.15 | 49.84 | 3.3 | 97.59 | 110.55 | 48.76 | 4.95 |
| S4 | 117.64 | 107.39 | 52.37 | 4.36 | 102.89 | 106.25 | 52.65 | 4.67 |
| S5 | 123.18 | 107.35 | 53.14 | 1.38 | 99.18 | 106.72 | 51.3 | 1.09 |
| S6 | 121.27 | 108.85 | 53.14 | 1.64 | 93.86 | 105.6 | 55.34 | 5.72 |
| S7 | 123.48 | 105.57 | 51.9 | 2.53 | 97.13 | 105.16 | 50.5 | 2.5 |
| S8 | 122 | 108.18 | 50.29 | 2.27 | 102.1 | 105.89 | 50.35 | 4.22 |
| Mean | 121.99 | 107.54 | 52.47 | 2.5 | 98.3 | 106.82 | 51.95 | 3.9 |
| STD | 2 | 0.97 | 1.79 | 0.99 | 3.33 | 1.83 | 2.41 | 1.58 |
| SEM | 0.71 | 0.34 | 0.63 | 0.35 | 1.18 | 0.65 | 0.85 | 0.56 |

TABLE 4

Atlas coordinates transformed from spatial coordinates of the final DBS positions that are acquired with postoperative CT scans using demons algorithm.
Atlas Coordinates Transformed by the Demons Algorithm (in unit of mm)

| Sub-ject | Left | | | | Right | | | |
|---|---|---|---|---|---|---|---|---|
| | X | Y | Z | Dc | X | Y | Z | Dc |
| S1 | 123.01 | 107.65 | 53.81 | 1.74 | 95.38 | 107.6 | 54.73 | 3.4 |
| S2 | 121.44 | 104.86 | 55.42 | 2.65 | | | | |
| S3 | 123.34 | 107.13 | 51.63 | 2.37 | 96.98 | 108.94 | 50.04 | 4.02 |
| S4 | 118.54 | 108.08 | 52.62 | 3.76 | 100.79 | 107.41 | 53.52 | 3.08 |
| S5 | 122.76 | 106 | 54.46 | 1.51 | 98.97 | 105.68 | 52.97 | 1.19 |
| S6 | 120.59 | 106.68 | 53.91 | 1.4 | 94.08 | 104.35 | 56.14 | 5.41 |
| S7 | 122.9 | 104.15 | 53.56 | 2.54 | 97.5 | 104.37 | 52.36 | 2.09 |
| S8 | 122.2 | 107.04 | 51.3 | 2.15 | 102.08 | 105.93 | 50.75 | 4.67 |
| Mean | 121.85 | 106.45 | 53.34 | 2.26 | 97.97 | 106.33 | 52.93 | 3.41 |
| STD | 1.62 | 1.36 | 1.4 | 0.76 | 2.86 | 1.73 | 2.13 | 1.46 |
| SEM | 0.57 | 0.48 | 0.5 | 0.27 | 1.01 | 0.61 | 0.75 | 0.52 |

The tighter the cluster of the projected atlas points of the DBS positions in the atlas is, the better the results are. Therefore, using the intra-operative coordinates according to the present invention to predict an initial target position will lead better results than using the post-operative CT coordinates. One explanation for this discovery is that the spread of the clusters in the atlas increases if measurement noise in the DBS positions used to create this atlas also increases. The sources of error associated with the post-operative DBS coordinates involve the centroid detection algorithm and the errors associated with registering pre-operative and post-operative CT images. The difference is the surgical placement error, i.e, the distance between the target point chosen intra-operatively and the position of the permanent DBS.

In summary, when projected onto a common reference volume, optimal DBS positions result in tight clusters if these positions can be determined accurately in each individual patient. These results also show, albeit in an indirect way, that the coordinates acquired intra-operatively are more accurate than the coordinates acquired post-operatively, and suggest a high accuracy for use of a platform from which intro-operative coordinates of the final DBS are acquired.

Comparison Between Manually Selected and Atlas-Guided Initial Target Positions

Tables 5 and 6 presents the Euclidean distance between the final DBS position acquired intra-operatively and (a) the initial position chosen manually and pre-operatively by the neurosurgeon, (b) the initial position suggested by projecting the DBS position from the atlas onto each patient using the ABA algorithm and (c) the same as in (b) but using the demons algorithm. In Tables 5, the atlas used in this case has been generated with the intro-operative DBS coordinates, while the atlas used in this case has been generated with the postoperative CT coordinates in Table 6. In both Tables 5 and 6, Columns Left and Right represent locations of the bilateral DBS targets, i.e., column Left corresponds to the left side implantation of the DBS, while column Right corresponds to the right side implantation of the DBS. Sub-columns Manual is the distance of a manually chosen initial target position to a final target position in a specific side for an individual patient, while sub-columns Automatic computes the distances of a nonmanually selected initial target position to a final target position in a specific side for an individual patient using a nonrigid registration algorithm, which is either an ABA algorithm (sub sub-column ABA) or a demons algorithm (sub sub-column Demons).

TABLE 5

Distance between the initial position selected manually and automatically and the final position selected intra-operatively (the atlas used in this case has been generated with the intro-operative DBS coordinates).
Distances Between Original and Final DBS Position
(in unit of mm)

| Subject | Left | | | Right | | |
|---|---|---|---|---|---|---|
| | Manual | Automatic | | Manual | Automatic | |
| | | ABA | Demons | | ABA | Demons |
| S1 | 5.95 | 2.58 | 2.4 | 6.94 | 3.52 | 2.94 |
| S2 | 5.72 | 1.78 | 3.39 | | | |
| S3 | 2.53 | 2.41 | 1.5 | 4.49 | 2.45 | 2.23 |
| S4 | 5.3 | 2.46 | 2.8 | 1.99 | 3.24 | 2.36 |
| S5 | 2.31 | 2.17 | 1 | 3.64 | 1.6 | 1.51 |
| S6 | 5.95 | 2.36 | 2.85 | 7.31 | 3.39 | 3.84 |
| S7 | 2 | 1.64 | 2.37 | 2.01 | 1.75 | 1.68 |
| S8 | 1.71 | 1.75 | 0.7 | 1.67 | 2.94 | 3.67 |
| Mean | 3.93 | 2.14 | 2.13 | 4.01 | 2.7 | 2.6 |
| STD | 1.94 | 0.37 | 0.96 | 2.36 | 0.78 | 0.91 |
| SEM | 0.69 | 0.13 | 0.34 | 0.83 | 0.28 | 0.32 |

Table 5 demonstrates that on the data sets used in this study, an atlas-guided placement of DBS is not only feasible but also is better than the technique in current clinical use. With both ABA and demons registration algorithms, the initial target points are substantially closer to the final ones than the initial target point chosen manually. It is shown that the average distance between an initial position selected with the automatic method and a final position of a DBS is 45% smaller on the left side and 30% on the right, respectively, than the one between an initial position selected manually and a final position of a DBS. Despite the small size of the data sets employed in the study, the distance between the initial target points and the final target points is significantly smaller (P<0.01, one sided paired t-test) than the distance between the initial target points chosen manually and the final target points for both ABA and demons algorithms on the left side. On the right side, the significance is only slightly smaller (P<0.07) and (P<0.06) for the ABA and demons algorithms, respectively. A comparison of Tables 5 and 6 also reveals critical information: when using the post-operative CT coordinates to create the atlas, atlas-guided placement of DBS does not do any better than the current manual approach. This is consistent with what is reported in Tables 1–4 that show tighter clusters with the intra-operative coordinates than with the post-operative CT coordinates.

TABLE 6

Distance between the initial position selected manually and automatically and the final position selected intra-operatively (the atlas used in this case has been generated with the post-operative CT coordinates).
Target Prediction Errors Post-operative Atlas
(in unit of mm)

| Subject | Left | | | Right | | |
|---|---|---|---|---|---|---|
| | Manual | Automatic | | Manual | Automatic | |
| | | ABA | Demons | | ABA | Demons |
| S1 | 5.95 | 1.69 | 1.74 | 6.94 | 4.11 | 3.4 |
| S2 | 5.72 | 2.87 | 3.69 | | | |
| S3 | 2.53 | 5.05 | 3.64 | 4.49 | 5.67 | 5.23 |
| S4 | 5.3 | 3.71 | 4.16 | 1.99 | 3.55 | 2.54 |
| S5 | 2.31 | 2.02 | 2.05 | 3.64 | 1.31 | 1.42 |
| S6 | 5.95 | 2.41 | 2.2 | 7.31 | 6.56 | 6.27 |
| S7 | 2 | 4.12 | 4.07 | 2.01 | 4.22 | 3.7 |
| S8 | 1.71 | 2.89 | 2.74 | 1.67 | 4.46 | 5.45 |
| Mean | 3.93 | 3.09 | 3.04 | 4.01 | 4.27 | 4 |
| STD | 1.94 | 1.13 | 0.97 | 2.36 | 1.66 | 1.73 |
| SEM | 0.69 | 0.4 | 0.34 | 0.83 | 0.59 | 0.61 |

Further Observations and Discussions

In the present invention, among other things, a fully automatic method for DBS target identification is disclosed. With both ABA and demons algorithms, the final positions of the deep brain stimulators, when mapped onto the atlas, lead to tight clusters with average point-to-centroid distance in the order of 1.5 voxel. The initial target points selected by the atlas and the nonrigid (ABA and demons) algorithms are substantially closer to the final ones than the initial target point chosen manually. The average distance between an initial position selected with the automatic method and a final position of a DBS is 45% smaller on the left side and 30% on the right, respectively, than the one between an initial position selected manually and a final position of a DBS. Despite the small size of the data sets employed in the study, the distance between the initial target points selected automatically and the final target points is significantly smaller (P<0.01, one sided paired t-test) than the distance between the initial target points chosen manually and the final target points for both ABA and demons algorithms on the left side. On the right side, the significance drops to (P<0.07) and (P<0.06) for the ABA and the demons algorithms, respectively.

Atkinson et al. [13] have also explored the idea of using an atlas for movement disorder related surgery. This group correlated the clinical efficacy of stereotactic thalamotomy for tremor with anatomical localization by using postoperative magnetic resonance (MR) imaging and a deformable atlas of subcortical structures. These authors have been able to demonstrate a significant difference in the position of the lesion in their atlas for patients in three clinical outcome groups: excellent, good, and fair. However, they do not provide data in which the position of the lesion predicted by the atlas can be quantitatively compared to either the initial position selected by the neurosurgeon or the final position chosen intra-operatively. Other differences include the fact that their procedure is performed with a stereotactic frame and that they rely on a lesion to eliminate the tremor rather than an implantable stimulator.

A number of issues remain to be investigated. Because the number of patients for gathering the necessary data is limited, the method has been evaluated on the set of data used to create the atlas. This may bias the results in the favor of the method or not. As the number of data sets increase, a separation of the image volumes into training and testing set may address this issue. The best way to develop the atlas also remains an area of investigation. In the current study one image volume is arbitrarily chosen as the atlas, which the impact of this choice on the results is unaddressed yet. A better approach may be to use a synthesized average image as the atlas. Additionally, all the image volumes are employed in the study regardless of clinical outcome. An alternative approach may be to select only cases for which the clinical outcome is excellent to build the atlas. However, none of these issues affect the utilization of the present invention.

The results presented herein may have a significant impact on the availability of the procedure. It is estimated that in the US alone 10–20,000 patients would benefit from DBS implantation each year. This number of procedures cannot be performed in leading research institution alone in which neurosurgeons have years of experience selecting targets manually. It is hoped that computer-assistance in target identification might make this procedure easier to perform by less experienced surgeons and hence make it available to many patients to whom it would otherwise remain inaccessible.

While there has been shown several and alternate embodiments of the present invention, it is to be understood that certain changes can be made as would be known to one skilled in the art without departing from the underlying scope of the invention as is discussed and set forth above and below. Furthermore, the embodiments described above are only intended to illustrate the principles of the present invention and are not intended to limit the scope of the invention to the disclosed elements.

List of References

[1]. Referen G. Deuschl, J. Volkmann, and P. Krack, "Deep brain stimulation for movement disorders", *Movement Disorders*, vol. 17 (supplement 3), pp S1-S1, 2002.

[2]. B. Schrader, W. Hamel, D. Weinert, and H. M. Mehdorn, "Documentation of electrode localization." *Movement Disorders*, vol. 17 (supplement 3), pp S167–S174, 2002.

[3]. J. L. Vitek, Mechanisms of deep brain stimulation: excitation or inhibition. *Movement Disorders*, vol. 17 (supplement 3), pp S69–S72, 2002.

[4]. A. M. Lozano, Deep brain stimulation for Parkinson's disease. Vol. 7, no. 3, pp 199–203, 2001.

[5]. R. L. Galloway and R. J. Maciunas, "Stereotactic neurosurgery", *Crit Rev Biomed Eng*, vol. 18, no. 3, pp 181–205, 1990.

[6]. J. Franck, P. Konrad, R. Franklin, F. Haer, and D. Hawksley. "STarFix: A Novel Approach to Frameless Stereotactic Neurosurgery Utilizing a Miniaturized Customized Pretargeted Cranial Platform Fixture—Technical Description, Unique Features, and Case Reports", *Movement Disorders Society*, 7th Intl. Congress of Parkinsons Disease & Movement Disorder, Miami, Fla., November 2002.

[7]. C. R. Maurer, Jr., J. M. Fitzpatrick, M. Y. Wang, R. L. Galloway, Jr., R. J. Maciunas, and G. S. Allen, "Registration of head volume images using implantable fiducial markers," *IEEE Trans. Med. Imaging*, vol. 16, pp 447–462, 1997.

[8]. J. P. Thirion, "Image matching as a diffusion process: an analogy with Maxwell's demons". *Medical Image Analysis*, vol. 2, no. 3, pp 243–260, 1998.

[9]. G. Rhode, A. Aldroubi and B. M. Dawant, "The Adaptive-bases algorithm for intensity-based nonrigid image registration," *IEEE Transactions on Medical Imaging*, vol. 22, no. 11, pp 1470–1479, 2003.

[10]. D. Rueckert, L. I. Sonoda, C. Hayes, D. L. G. Hill, M. O. Leach, and D. J. Hawkes, "Nonrigid Registration Using Free-Form Deformations: Application to Breast MR Images." *IEEE Transactions on Medical Imaging*, vol. 18, no. 8, pp 712–721, 1999.

[11]. C. R. Meyer, J. L. Boes, B. Kim, P. Bland, K. R. Zasadny, P. V. Kison, K. Koral, K. A. Frey, and R. L. Wahl., "Demonstration of accuracy and clinical versatility of mutual information for automatic multimodality image fusion using affine and thin-plate" *Medical Image Analysis*, vol. 3, pp 195–206, 1997.

[12]. F. Maes, A. Collignon, and P. Suetens, "Multimodality image registration by maximization of mutual information," *IEEE Transaction on Medical Imaging* vol. 16, no. 2, pp 187–198, 1997.

[13]. J. D. Atkinson, D. L. Collins, G. Bertrand, T. M. Peters, G. B. Pike, and A. F. Sadikot, "Optimal location of thalamotomy lesions for tremor associated with Parkinson Disease: a probabilistic analysis based on postoperative magnetic resonance imaging and an integrated digital atlas", *J. Neurosurgery*, vol. 96, pp 854–866, 2002.

[14]. G. Schaltenbrand and W. Wahren, *Atlas for Stereotaxy of the Human Brain*. Stuttgart, Germany: Thieme, 1977.

[15]. K. W. Finnis, Y. P. Starreveld, A. G. Parrent, A. F. Sadikot, and T. M. Peters, "Three-dimensional database of dubcortical dlectrophysiology for dmage-guided stereotactic functional neurosurgery", *IEEE Transactions on Medical Imaging*, vol. 22 (11), pp 93–104, 2003.

[16]. J. Talairach and P. Tourneau, *Co-Planar Stereotaxic Atlas of the Human Brain*. Stuttgart, Germany: Georg Thieme Verlag, 1988.

[17]. P. St-Jean, A. F. Sadikot, D. L. Collins, D. Clonda, R. Kasrai, A. C. Evans, and T. M. Peters, "Automated atlas integration and interactive 3-dimensional visualization tools for planning and guidance in functional neurosurgery," *IEEE Trans. Med. Imag.*, vol. 17, pp 672–680, 1998.

[18]. G. Deuschl, J. Volkmann, P. Krack, "Deep brain stimulation for movement disorders", *Movement Disorders*, vol. 17 (supplement 3) pp, S1-S1, 2002.

[19]. Deuschl, G., et al., "Deep brain stimulation of the subthalamic nucleus for Parkinson's disease: a therapy approaching evidence-based standards." *J Neurol*, 2003. 250 Suppl 1: p. I43–I46.

[20]. B. Horn and B. Schunck, "Determining optical flow", *Artificial Intelligence*, vol. 17, pp. 185–203, 1981.

[21]. D. J. Burr, "A dynamic model for image registration." *Computer Graphics and Image Processing*, vol. 15, pp. 102–112, 1981.

[22]. C. Nickele, E. Cetinkaya, J. Michael Fitzpatrick, and P. E. Konrad. "Method for Placing Deep-Brain Stimulators", Proceedings of *Medical Imaging* 2003: *Image Processing*, SPIE, (in press).

What is claimed is:

1. A method for optical placement of a deep brain stimulator in a targated region of a brain of a living subject, comprising the steps of nonmanually selecting an initial optimal position from which a final position for optimal placement of a deep brain stimulator in the targrted region is determined, wherein the step of nonmanually selecting the initial optimal position comprises the steps of:

a. choosing an image volume as a common volume of reference from a set of image volumes, the set of image volumes having N image volumes each being acquired pre-operatively from a brain of a living subject having a deep brain stimulator placed in a target, N being an integer greater than 2;

b. registering each of the remaining N−1 image volumes to the chosen common volume of reference by a nonrigid registration algorithm so as to create an atlas;

c. mapping spatial coordinates of the deep brain stimulator in each of the remaining N−1 image volumes onto atlas coordinates in the atlas by a transformation that registers the corresponding image volume to the atlas;

d. computing a centroid of all the mapped atlas coordinates as an optimal target position of the deep brain stimulator in the atlas; and e. projecting the optimal target position of the deep brain stimulator in the atlas onto the pre-operatively acquired image volume by an inverse of the transformation that registers the pre-operatively acquired image volume to the atlas so as to identify the initial optimal position of the deep brain stimulator in the targeted region of the brain of the living subject.

2. The method of claim 1, wherein the spatial coordinates of the deep brain stimulator are acquired intra-operatively by a guidance system that translates physical coordinates of the deep brain stimulator into coordinates of the pre-operative image volume.

3. The method of claim 1, wherein the spatial coordinates of the deep brain stimulator are acquired post-operatively by CT scans.

4. The method of claim 1, wherein the nonrigid registration algorithm for registering a source image volume to a target image volume comprises a demons algorithm that computes a transformation that minimizes the voxel-by-voxel intensity difference between the source image volume and the target image volume.

5. The method of claim 1, wherein the nonrigid registration algorithm for registering a source image volume to a target image volume comprises an adaptive base algorithm.

6. The method of claim 5, wherein the adaptive base algorithm comprises the steps of:

a. defining a source image corresponding to one of the remaining N−1 image volumes;

b. defining a target image corresponding to the atlas;

c. creating an image pyramid for each of the source image and the target image, respectively, each image pyramid having M levels, wherein each level of the image pyramid has a resolution and is segmented with a corresponding scale so as to form a grid, each pyramid being formed such that level i of the pyramid has lower resolution and larger scale than level (i−1), i=1, . . . , M, M being an integer greater than 1;

d. defining a deformation field, v(x), that registers the source image volume to the target image volume;

e. initializing the deformation field, $v(x)=v_M(x)$;

f. computing the deformation field, $v_i(x)$, at level i of the image pyramids, wherein the deformation field $v_i(x)$ at the level i is a sum of the deformation field at level (i+1) and a linear combination of a set of radial basis functions spaced on the grid of level i so as to register the source image volume to the target image volume at level i, and wherein the computing starts at level (M−1);

g. identifying regions of misregistration resulted from step (f);

h. optimizing each of the regions of misregistration independently from each other by modifying the region of support and radial basis functions corresponding to the region in the deformation field $v_i(x)$; and i. iterating steps (f)–(h) at a next level (i−1) of the image pyramids till level 1 is reached so as to construct a final deformation field in the form of:

$v(x)=v_1(x)+ \ldots +v_M(x)$.

7. The method of claim 6, further comprising the step of:
optimizing a constraint scheme for enforcing a Jacobian matrix of the deformation field to remain uniformly invertible throughout a domain of the source image volume and a corresponding domain of the target image volume so as to generate topologically correct transformations between the source image volume and the target image volume.

8. The method of claim 1, wherein the atlas is a common volume of reference in which the position of each deep brain stimulator can be recorded.

9. A method for optical placement of a deep brain stimulator in a targated region of a brain of a living subject, comprising the steps of:

i. nonmanually selecting an initial optimal position in the targeted region;

ii. finding a final position from the nonmanually selected initial optimal position; and iii. placing the deep brain simulator at the final position; wherein the step of nonmanually selecting the initial optimal position comprises the steps of:

a. choosing an image volume as a common volume of reference from a set of image volumes, the set of image volumes having N image volumes each being acquired pre-operatively from a brain of a living subject having a deep brain stimulator placed in a target, N being an integer greater than 2;

b. registering each of the remaining N−1 image volumes to the chosen common volume of reference by a nonrigid registration algorithm so as to create an atlas;

c. mapping spatial coordinates of the deep brain stimulator in each of the remaining N−1 image volumes onto atlas coordinates in the atlas by a transformation that registers the corresponding image volume to the atlas;

d. computing a centroid of all the mapped atlas coordinates as an optimal target position of the deep brain stimulator in the atlas; and e. projecting the optimal target position of the deep brain stimulator in the atlas onto the pre-operatively acquired image volume by an inverse of the transformation that registers the pre-operatively acquired image volume to the atlas so as to identify the initial optimal position of the deep brain stimulator in the targeted region of the brain of the living subject.

10. The method of claim 9, wherein the spatial coordinates of the deep brain stimulator are acquired intra-operatively by a positioning drive that translates physical coordinates of the deep brain stimulator into coordinates of the pre-operative image volume.

11. The method of claim 9, wherein the spatial coordinates of the deep brain stimulator are acquired post-operatively by CT scans.

12. The method of claim 9, wherein the nonrigid registration algorithm comprises a demons algorithm that computes a transformation that minimizes the voxel-by-voxel intensity difference between the images.

13. The method of claim 9, wherein the nonrigid registration algorithm comprises an adaptive base algorithm.

14. The method of claim 13, wherein the adaptive base algorithm comprises the steps of:
  a. defining a source image corresponding to one of the remaining N−1 image volumes;
  b. defining a target image corresponding to the atlas;
  c. creating an image pyramid for each of the source image and the target image, respectively, each image pyramid having M levels, wherein each level of the image pyramid has a resolution and is segmented with a corresponding scale so as to form a grid, each pyramid being formed such that level i of the pyramid has lower resolution and larger scale than level (i−1), i=1, ..., M, M being an integer greater than 1;
  d. defining a deformation field, v(x), that registers the source image volume to the target image volume;
  e. initializing the deformation field, $v(x)=v_M(x)$;
  f. computing the deformation field, $v_i(x)$, at level i of the image pyramids, wherein the deformation field $v_i(x)$ at the level i is a sum of the deformation field at level (i+1) and a linear combination of a set of radial basis functions spaced on the grid of level i so as to register the source image volume to the target image volume at level i, and wherein the computing starts at level (M−1);
  g. identifying regions of misregistration resulted from step (f);
  h. optimizing each of the regions of misregistration independently from each other by modifying the region of support and radial basis functions corresponding to the region in the deformation field $v_i(x)$; and
  i. iterating steps (f)–(h) at a next level (i−1) of the image pyramids till level 1 is reached so as to construct a final deformation field in the form of:

$$v(x)=v_1(x)+ \ldots +v_M(x).$$

15. The method of claim 14, further comprising the step of:
  optimizing a constraint scheme for enforcing a Jacobian matrix of the deformation field to remain uniformly invertible throughout a domain of the source image volume and a corresponding domain of the target image volume so as to generate topologically correct transformations between the source image volume and the target image volume.

16. The method of claim 9, wherein the atlas is a common volume of reference in which the position of each deep brain stimulator can be recorded.

17. An apparatus of optical placement of a deep brain simulator in a targeted region of a brain of a living subject, comprising a controller performing the step of nonmanually selecting an initial optimal position from which a final position for optical placement of deep brain simulator in the targeted region is determinated, wherein the controler furter performing the steps of:
  a. choosing an image volume as a common volume of reference from a set of image volumes, the set of image volumes having N image volumes each being acquired pre-operatively from a brain of a living subject having a deep brain stimulator placed in a target, N being an integer greater than 2;
  b. registering each of the remaining N−1 image volumes to the chosen common volume of reference by a nonrigid registration algorithm so as to create an atlas;
  c. mapping spatial coordinates of the deep brain stimulator in each of the remaining N−1 image volumes onto atlas coordinates in the atlas by a transformation that registers the corresponding image volume to the atlas;
  d. computing a centroid of all the mapped atlas coordinates as an optimal target position of the deep brain stimulator in the atlas; and
  e. projecting the optimal target position of the deep brain stimulator in the atlas onto the pre-operatively acquired image volume by an inverse of the transformation that registers the pre-operatively acquired image volume to the atlas so as to identify the initial optimal position of the deep brain stimulator in the targeted region of the brain of the living subject.

18. The apparatus of claim 17, wherein the spatial coordinates of the deep brain stimulator are acquired intra-operatively by a guidance system that translates physical coordinates of the deep brain stimulator into coordinates of the pre-operative image volume.

19. The apparatus of claim 17, wherein the spatial coordinates of the deep brain stimulator are acquired post-operatively by CT scans.

20. The apparatus of claim 17, wherein the nonrigid registration algorithm comprises a demons algorithm that computes a transformation that minimizes the voxel-by-voxel intensity difference between the images.

21. The apparatus of claim 17, wherein the nonrigid registration algorithm comprises an adaptive base algorithm.

22. The apparatus of claim 21, wherein the adaptive base algorithm comprises the steps of:
  a. defining a source image corresponding to one of the remaining N−1 image volumes;
  b. defining a target image corresponding to the atlas;
  c. creating an image pyramid for each of the source image and the target image, respectively, each image pyramid having M levels, wherein each level of the image pyramid has a resolution and is segmented with a corresponding scale so as to form a grid, each pyramid being formed such that level i of the pyramid has lower resolution and larger scale than level (i−1), i=1, ..., M, M being an integer greater than 1;
  d. defining a deformation field, v(x), that registers the source image volume to the target image volume;
  e. initializing the deformation field, $v(x)=v_M(x)$;
  f. computing the deformation field, $v_i(x)$, at level i of the image pyramids, wherein the deformation field $v_i(x)$ at the level i is a sum of the deformation field at level (i+1) and a linear combination of a set of radial basis functions spaced on the grid of level i so as to register the source image volume to the target image volume at level i, and wherein the computing starts at level (M−1);
  g. identifying regions of misregistration resulted from step (f);
  h. optimizing each of the regions of misregistration independently from each other by modifying the region of support and radial basis functions corresponding to the region in the deformation field $v_i(x)$; and
  iterating steps (e)–(g) at a next level (i−1) of the image pyramids till level 1 is reached so as to construct a final deformation field in the form of:

$$v(x)=v_1(x)+ \ldots +v_M(x).$$

23. The apparatus of claim 22, wherein the adaptive base algorithm further comprises the step of:

optimizing a constraint scheme for enforcing a Jacobian matrix of the deformation field to remain uniformly invertible throughout a domain of the source image volume and a corresponding domain of the target image volume so as to generate topologically correct transformations between the source image volume and the target image volume.

24. The apparatus of claim 17, wherein the atlas is a common volume of reference in which the position of each deep brain stimulator can be recorded.

* * * * *